United States Patent
Leiner et al.

(10) Patent No.: US 8,641,416 B2
(45) Date of Patent: Feb. 4, 2014

(54) SYRINGE AND METHOD FOR DOSED DISPENSING OF MATERIALS

(75) Inventors: Uwe Leiner, Midlum (DE); Manfred T. Plaumann, Cuxhaven (DE)

(73) Assignee: VOCCO GmbH, Cuxhaven (DE)

( * ) Notice: Subject to any disclaimer, the term of this patent is extended or adjusted under 35 U.S.C. 154(b) by 1255 days.

(21) Appl. No.: 12/175,934

(22) Filed: Jul. 18, 2008

(65) Prior Publication Data
US 2009/0047622 A1 Feb. 19, 2009

(30) Foreign Application Priority Data

Jul. 20, 2007 (DE) .......................... 10 2007 034 477

(51) Int. Cl.
*A61C 5/04* (2006.01)
(52) U.S. Cl.
USPC .......................................................... 433/90
(58) Field of Classification Search
USPC ..................... 433/80–90; 604/278, 218, 219, 604/220–223, 226, 228, 229
See application file for complete search history.

(56) References Cited

U.S. PATENT DOCUMENTS

| | | | |
|---|---|---|---|
| 812,686 A * | 2/1906 | Schork et al. | 604/222 |
| 1,687,091 A * | 10/1928 | Hein | 604/221 |
| 1,712,069 A | 5/1929 | Cressler | |
| 2,902,035 A | 10/1958 | Hartley | |
| 3,661,152 A | 5/1972 | Beich | |
| 3,766,918 A | 10/1973 | Kessel | |
| 3,874,382 A * | 4/1975 | Nogier et al. | 604/222 |
| 4,266,557 A * | 5/1981 | Merry | 600/576 |

(Continued)

FOREIGN PATENT DOCUMENTS

DE 20 25 379 A1 12/1971
DE 43 32 308 9/1993

(Continued)

OTHER PUBLICATIONS

Office Action in parallel European application 08 160 772.3 dated Aug. 19, 2011.

*Primary Examiner* — Cris L Rodriguez
*Assistant Examiner* — Mirayda A Aponte
(74) *Attorney, Agent, or Firm* — Roylance, Abrams, Berdo & Goodman, L.L.P.

(57) ABSTRACT

A syringe (1) for dosed dispensing of material, in particular of free-flowing and/or pasty dental material, includes a sleeve (10) for accommodating material and a piston (15) which can be inserted into the sleeve (10) and which has a piston member (15'), a frictional engagement element (25) which abuts an inner wall (35) of the sleeve (10), and an elastic element (30) coupling the frictional engagement element (25) and the piston 10 member (15'), wherein the sleeve (10) and the piston (15) inserted into the sleeve define an inner sleeve chamber (70) for accommodating the material, wherein the elastic element (30) can be tensioned, on insertion of the piston (15) and/or of the piston member (15') into the sleeve (10), by means of a relative lag of the frictional engagement element (25) in relation to the piston member (15'), 15 wherein by relaxing the elastic element (30) it is possible for the piston member (15') to be expelled at least partially from the sleeve (10) while the frictional engagement element (25) remains motionless, in order to increase the volume of the inner sleeve chamber (70). A corresponding method dispenses a material using a piston (15) and a frictionally engaging elastic element (20).

21 Claims, 16 Drawing Sheets

(56) References Cited

U.S. PATENT DOCUMENTS

Figure 1A:
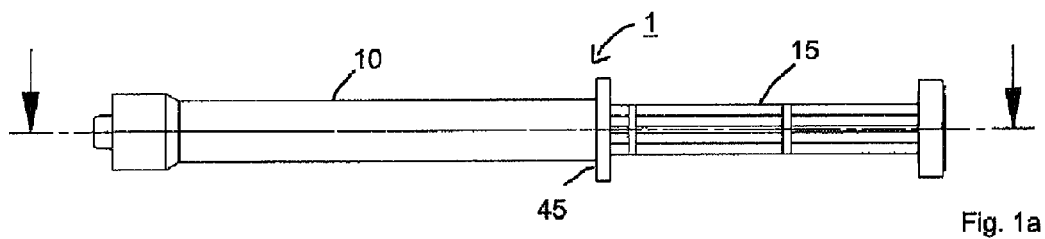

| | | | | |
|---|---|---|---|---|
| 5,549,573 | A * | 8/1996 | Waskonig | 604/218 |
| 6,749,590 | B2 * | 6/2004 | Niedospial, Jr. | 604/218 |
| 7,491,191 | B2 * | 2/2009 | Wagner et al. | 604/228 |
| 2003/0035744 | A1 * | 2/2003 | Horita et al. | 417/460 |
| 2005/0182371 | A1 * | 8/2005 | Wagner et al. | 604/218 |
| 2008/0125723 | A1 | 5/2008 | Leiner | |

FOREIGN PATENT DOCUMENTS

| | | |
|---|---|---|
| DE | 42 19 502 A1 | 12/1993 |
| DE | 199 45 397 | 9/1999 |
| DE | 699 22 027 | 10/2005 |
| DE | 602 12 527 T2 | 6/2007 |
| EP | 0064858 | 5/1982 |
| FR | 1 108 413 A | 1/1956 |

* cited by examiner

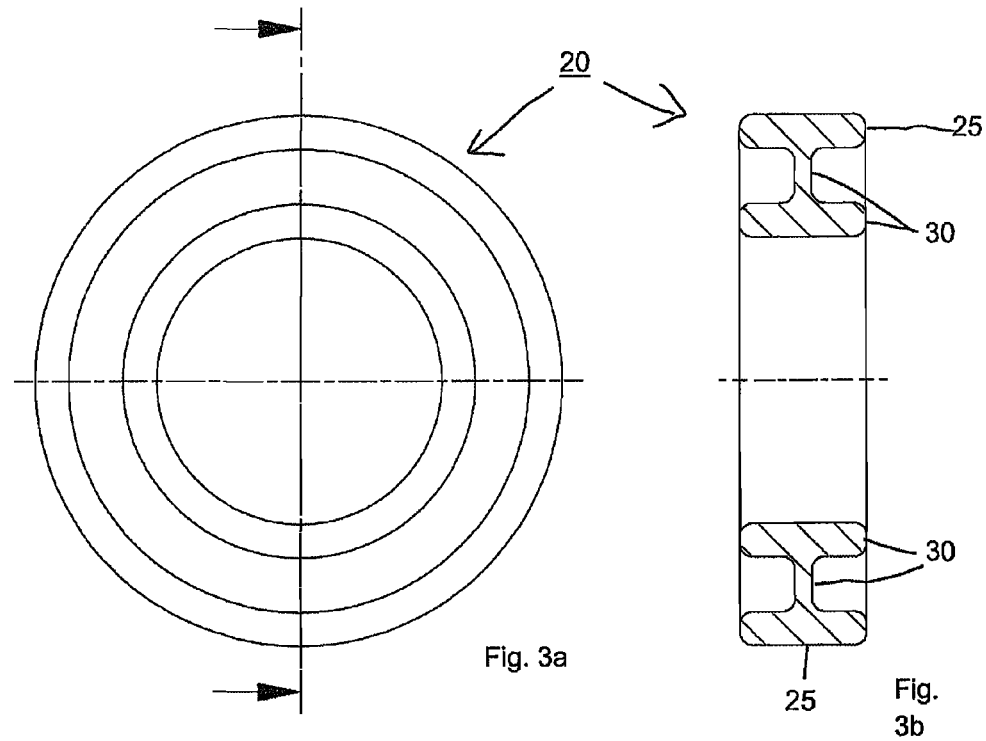
Fig. 3a
Fig. 3b
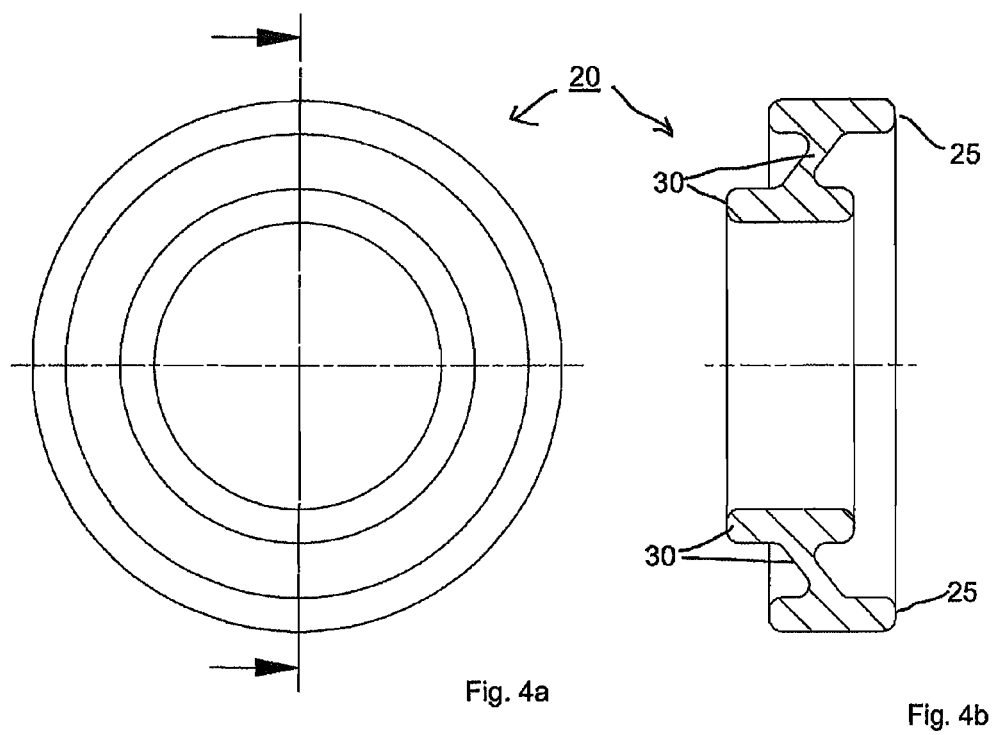
Fig. 4a
Fig. 4b

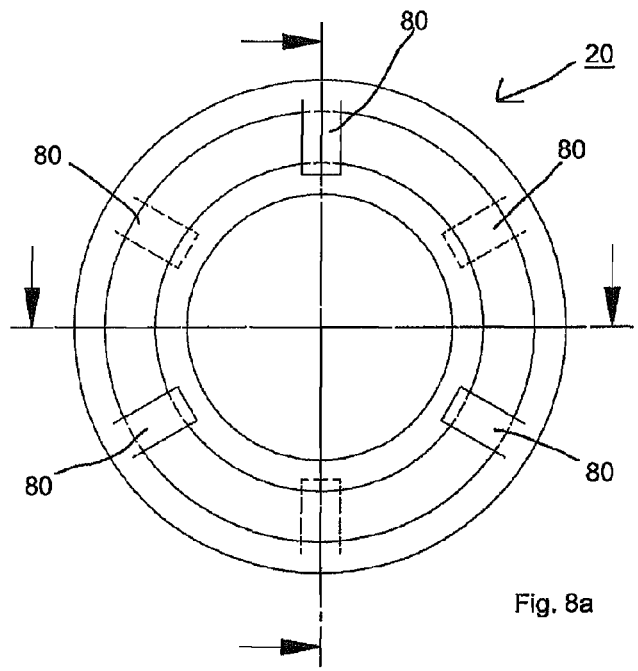
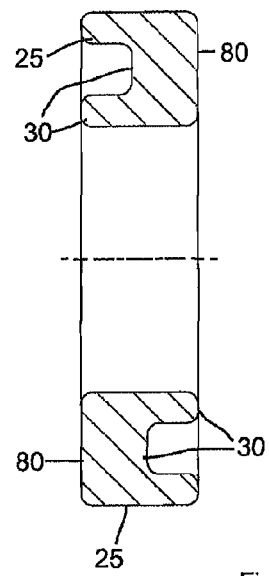
Fig. 8a
Fig. 8b
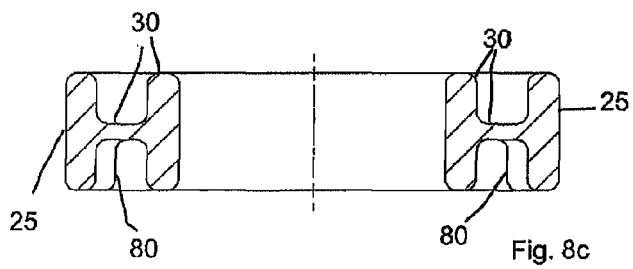
Fig. 8c
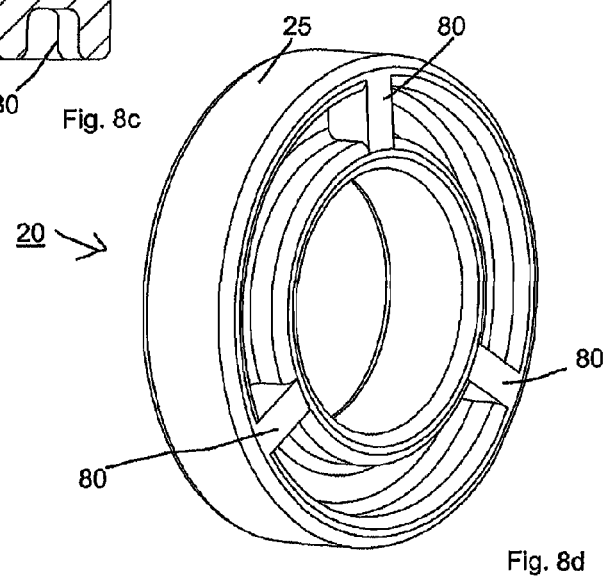
Fig. 8d

SYRINGE AND METHOD FOR DOSED DISPENSING OF MATERIALS

The present invention relates to a syringe and a method for dosed dispensing of materials, in particular (but not exclusively) of free-flowing and/or pasty dental materials.

Various filling materials are used in the dental field. The viscosities of these materials range from very solid, stuffable composites to so-called flow materials having a fluid consistency. Flow materials are usually placed on the market in prefilled syringes. Such a syringe contains material for many applications. Normally, disposable needles are also provided which permit targeted administration to a tooth to be treated.

In other fields also, free-flowing and/or pasty materials are dispensed from a syringe or similar device. Examples can be found in soldering, in the application of pastes such as a thermal paste, or very generally in the dispensing or application of adhesives. Further examples include commercial 2-component systems such as silicone sealing systems using "Euro-cartridges", Mixpac syringes and cartridges, and other adhesive systems.

Syringes are described in documents DE 26 44 930, DE 39 30 817, DE 42 00 044, DE 43 32 307, DE 43 32 310, DE 89 04 429, DE 699 22 027 T2, EP 0 472 023, EP 0 645 122, JP 2000-344282, JP 02-077247, U.S. Pat. No. 3,853,125, U.S. Pat. No. 4,863,072, U.S. Pat. No. 5,697,918 and US 2005/0222539, for example.

The disadvantage of known syringes is that the material tends to continue flowing after pressure on the plunger or piston is released. This means that free-flowing material escapes from a needle, which is provided for application, also after pressure on the piston is released. A small drop forms at the end of the needle and, depending on its size, can drip down and contaminate the working area. In the dental field, in particular, this is a great annoyance for a dentist providing treatment, since this contaminated area of the treatment table must be cleaned using suitable, usually strong, solvents. In addition, the needle must be wiped before further use on the same patient, which means additional effort. Another aspect is that material dispensed from the syringe does not detach itself completely from the needle after exiting the needle. This results in a drop forming in the region around the end of the needle, even when no additional material is discharged. As a residue of material intentionally discharged from the needle but which remains attached to the needle, this drop can lead to undesired contamination.

A syringe made by Kuraray, the Japanese manufacturer, is known, in which an O-ring is used for sealing. The syringe plunger has a number of bulges on small areas of the surface pushing the O-ring, which are intended to penetrate the O-ring elastically when a force is applied to the plunger. When pressure on the device is released, the O-ring presumably springs back, thus causing a partial withdrawal of the syringe plunger from the sleeve of the syringe. This would cause a reverse suction effect, which would involve material being sucked back into the syringe. The functionality of this arrangement is severely restricted, however. On the one hand, the reverse suction effect is reduced in this way to only a small value, solely due to the configuration of the arrangement and the limited deformability of the O-ring. Furthermore, the deformed O-ring has two possibilities for restoring its shape. A reverse suction effect is achieved only in the one case, in which the parts of the O-ring which penetrated between the bulges remain stationary and drive the syringe plunger back when the remaining part of the O-ring is pulled back. The other possibility is that the parts between the bulges of the driving face of the O-ring are pulled back to the non-penetrating parts, as a result of which no reverse suction effect is caused, at best, but in the worst case even causing the syringe plunger to be driven into the syringe. The O-ring abuts the outer side of the syringe plunger and the inner side of the syringe sleeve over the entire area in each case, the type of restoration being determined by the local frictional forces and is therefore left mainly to chance.

In EP 0 645 122, an arrangement is proposed for use with highly viscous materials in rotary syringes, comprising a membrane that in the resting state is outwardly domed in the direction of the longitudinal axis in relation to an inner syringe chamber. According to EP 0 645 122, the rotating piston driven forwards on application of material causes deformation of the membrane such that it "flips" in the direction of the syringe inner chamber. After application of the material, the rotating piston is withdrawn so that pressure on the membrane is relieved, thus permitting restoration of the membrane to its original state. It is disadvantageous here that, when applying material, it is not determined whether the membrane as a whole is displaced without deforming the membrane, or whether deformation of the membrane leads to application of material. In addition, it is necessary that the rotating piston be turned back manually by the user, which leads to the material in the syringe inner chamber being relieved of pressure, even without a separate membrane.

Other syringes are known from U.S. Pat. No. 1,563,627, U.S. Pat. No. 1,948,982, U.S. Pat. No. 2,419,401, U.S. Pat. No. 2,526,365, U.S. Pat. No. 2,575,425, U.S. Pat. No. 2,902,034, U.S. Pat. No. 3,045,674, U.S. Pat. No. 3,618,603, U.S. Pat. No. 3,678,930, U.S. Pat. No. 3,766,918, U.S. Pat. No. 3,890,956, U.S. Pat. No. 4,363,329, U.S. Pat. No. 4,381,779, U.S. Pat. No. 4,543,093, U.S. Pat. No. 4,678,107, U.S. Pat. No. 4,986,820 and U.S. Pat. No. 6,796,217.

The object of the present invention is to provide a syringe and a method for dosed dispensing of materials, in which the afterdripping effect described above, especially in the case of medium and low-viscosity materials, does not occur at all or only to a reduced extent, and in which a desired, predeterminable and sufficiently large reverse suction effect occurs in a controlled and reproducible manner.

This object is achieved by a syringe for dosed dispensing of material, in particular of free-flowing and/or pasty dental material, comprising a sleeve for accommodating material and a piston which can be inserted into the sleeve and which comprises a piston member, a frictional engagement element which (in the operating state) abuts an inner wall of the sleeve, and an elastic element coupling the frictional engagement element and the piston member, wherein the sleeve and the piston inserted into the sleeve define an inner sleeve chamber for accommodating the material, wherein the elastic element can be tensioned on insertion of the piston and/or of the piston member into the sleeve by means of a relative lag of the frictional engagement element in relation to the piston member, wherein by relaxing the elastic element it is possible for the piston member to be expelled at least partially from the sleeve while the frictional engagement element remains motionless, in order to increase the volume of the inner sleeve chamber.

The object is also achieved by a method for dosed dispensing of materials, in particular of free-flowing and/or pasty dental materials, with a syringe comprising a sleeve for accommodating material and a piston which can be inserted into the sleeve and which comprises a piston member, a frictional engagement element which abuts an inner wall of the sleeve, and an elastic element coupling the frictional engagement element and the piston member, wherein the sleeve and the piston inserted into the sleeve define an inner sleeve chamber for accommodating the material, said method comprising the steps: providing a syringe filled at least partially with material, applying a force to the piston for bringing the piston and/or the piston member into the sleeve, in order to dispense doses of material from the syringe, tensioning the elastic element by means of a relative lag of the frictional engagement element relative to the piston member, ending the application of force to the piston, at least partially expelling the piston member from the sleeve while the frictional engagement element remains motionless, by relaxation of the elastic element, wherein an increase in the volume of the inner sleeve chamber is achieved by said expulsion, in order to prevent at least partially any undesired further dispensing of material.

In the method according to the invention, providing the syringe preferably comprises the steps: bringing the piston into the at least partially empty syringe, supplying material, and removing the piston in order to fill the syringe with material. The piston can be removed by withdrawing the piston (member) and/or by expelling the piston from the sleeve. The piston can be expelled by the material, by forcibly filling the syringe through the discharge opening.

In the syringe according to the invention, the sleeve, piston member, frictional engagement element and elastic element are arranged such that, when the piston and/or the piston member is inserted into the sleeve (for example due to manual application of force or by the action of a force on the piston member), the frictional engagement element lags relative to the piston member due to the frictional force acting between the frictional engagement element and the inner wall of the sleeve, the elastic element being tensioned as a result. The frictional force thus prevents, at least temporarily, the frictional engagement element from moving with the piston member when the piston or piston member is inserted. This means that less work is performed on the frictional engagement element compared to the piston member, wherein part of the work expended on insertion is stored in the tensioned elastic element.

The elastic element couples the frictional engagement element and the piston member with each other, such that a force exerted on the piston member so that it penetrates into the sleeve is transferred at least partially via the elastic element to the frictional engagement element, and that when the piston member is relieved of pressure, i.e. when the elastic element is relaxed, the frictional engagement element acts as a support for the elastic element, so that the elastic element at least partially expels the piston member when it relaxes.

For a coupling, it is not necessary that the elastic element connects the frictional engagement element and the piston member to each other in such a manner that, when the piston member is retracted, the frictional engagement element is pulled back with it via the elastic element. According to the invention, such a fixed coupling is not excluded, however.

The elastic element is configured in such a way that at least part of the energy input is absorbed as deformation energy and can be released against in the form of restoration, at least when actuating the piston, i.e. when the piston member penetrates into the sleeve.

When the application of force ends, i.e. when the piston or piston member is relieved of pressure, restoring forces come to bear as a result of the tensioned elastic element, such that the piston member is at least partially driven out of the sleeve against the direction of insertion. The energy stored in the elastic element on insertion of the piston or piston member and tensioning of the elastic element is used here to remove the piston member at least partially from the sleeve, resulting in enlargement of the inner space between sleeve and piston, in which the material to be applied is accommodated. This results in a reverse suction effect that can cause free-flowing material located outside the syringe in the region of the discharge opening of the sleeve to be sucked (back) in.

In a shear test conducted at 23° C. with plate-plate geometry, the free-flowing and/or pasty materials for which the inventive syringe and the inventive method is preferably provided has a viscosity range from 0.5 to 5000 Pa·s, in particular, at shear rates of 0.1 to 10 $s^{-1}$.

The amount of adhesive or sliding friction between the inner wall of the sleeve and the frictional engagement element can be set by means of suitable material pairs and adjustments to surface properties. The basic options in this context are known to a person skilled in the art, so a detailed description can be dispensed with. Particularly good results can be achieved with polyolefines (e.g. polypropylene PP or polyethylene PE), paired with silicones or elastomers. Other material pairs are likewise possible, however.

The frictional forces typically range in order from 0.1N to 10N. Stronger frictional forces make a stronger reverse suction effect possible. This is expedient in the case of materials of higher viscosity, in particular, so that the reverse suction effect is strong enough to be effective through the application needle (which may be narrow) as far as its outlet. Weaker frictional forces increase the convenience of using the syringe.

The elastic element is tensioned by the action of a shear force, a tensile force or a compressive force on the elastic element as a whole; depending on the specific configuration of the elastic element, other types of forces way also occur inside the elastic element. For example, in an elastic element that is configured like a known helical spring, for example, torsional stress may arise in the material, even when the elastic element as a whole does not absorb any tensile or compressive stress. Combinations of different types of forces and/or absorbed stress are likewise possible. For example, an elastic element may be subjected to a tensile and a shear force when tensioned.

Suitable examples of materials from which the elastic element can be made are: silicone, (thermoplastic-) elastomers, nitrile rubber (NBR), ethylene-propylene-diene rubber (EPDM) and the like. Silicones are especially preferred on account of their high elasticity and good chemical stability.

In one embodiment of the invention, the piston is provided with a sealing means that is configured to seal the piston with the inner wall of the sleeve against the passage of material (see, for example, FIG. 1c, 2c, 5c, 6c, 7c, 9c, 10c, 13c or 15c).

If the piston is provided with a sealing element, it is possible by this means to prevent the escape or passage of material out of the syringe past the piston, or at least to suppress such escape or passage to a sufficient extent. A separate sealing means permits a better sealing effect than the sealing effect that is assured merely by the small gap width between the piston and the sleeve.

In one advantageous embodiment of the invention, the sealing means is formed by the frictional engagement element, the elastic element or by a combination of frictional engagement element and elastic element.

The frictional engagement element, the elastic element or a combination of frictional engagement element and elastic element will preferably perform a double function and will additionally function as a sealing means; this permits simple assembly of the syringe according to the invention, without additional elements having to be provided, such as a separate sealing means.

Attention is drawn in this connection to the fact that, even when the frictional engagement element according to the invention frictionally abuts an inner wall or inner surface of the sleeve, this does not necessarily imply that the frictional engagement element abuts the inner wall over its entire circumference. It may also be provided that the frictional engagement element abuts the inner wall of the sleeve in sections therefore only, i.e. only in certain (sub-)areas thereof. A sufficient frictional force is ensured, even without engagement across the entire surface, when the material parameters are suitably chosen and when the inner wall and the frictional engagement element have a suitable geometry.

According to one advantageous embodiment, the elastic element couples the frictional engagement element and the piston member with each other (see, for example, FIG. 3b or 4b).

If the elastic element is used not only to generate a spring effect, but also and additionally to connect the frictional engagement element and the piston member, a simple transmission of force onto the piston member is achieved, wherein the frictional engagement element is used as a kind of counter-bearing for the force action, without additional elements being required. Other elements are also permitted, however.

By connecting the frictional engagement element and the piston member via the elastic element, it is also possible to fix the frictional engagement element and piston member relative to each other, in the sense that when the piston member is pulled out of the sleeve, for example, the frictional engagement element is removed as well from the sleeve by means of the elastic element. However, in the above embodiment it is not imperative that a fixed connection be provided between the elastic element, the frictional engagement element and the piston member. The connection may also derive solely from the elastic element being disposed between the frictional engagement element and the piston member, and thus serves as a connections between these elements.

According to another embodiment of the present invention, the elastic element is spaced apart from the inner wall of the sleeve by the frictional engagement element when the piston is inserted into the sleeve (see, for example, FIG. 1c, 2c, 5c, 6c, 7c, 9c, 10c, 13c or 15c).

If the frictional engagement element is located between the inner wall of the sleeve and the elastic element, and separates these from each other, it is not possible for the elastic element to be influenced directly by the inner wall. This ensures that a force acts on the elastic element only when there is relative movement between the frictional engagement element and the piston member when the piston or piston member is inserted into or pulled out of the sleeve, but not by a movement of the piston that does lead to a relative movement of the frictional engagement element and the piston member.

In one preferred embodiment of the invention, the frictional engagement element and the elastic element are configured as a single, integral element (as a frictionally engaging elastic element) (see, for example, FIG. 3a, 3b, 4a, 4b, or 8a-d).

When a frictionally engaging elastic element is embodied as an integral element that performs the function of the frictional engagement element as well as the function of the elastic element, it is possible to manufacture the frictional engagement element and the elastic element in a relatively simplified manner, in which it is possible to dispense with any connecting elements or connecting steps that might otherwise be necessary.

According to one advantageous embodiment, the elastic element is anchored to the piston member.

When the elastic element is fixed or fastened to the piston member, in particular when it is fixed against relative movement in the direction of the longitudinal axis of the syringe, it is possible to ensure, irrespective of any direction of movement, for example when inserting and removing the piston, that the elastic element and the piston member remain motionless in relation to each other (at least in the axial direction) and hence that they are always located in a desired positional relationship to each other.

Other possible examples of fixing the elastic element and piston member in relation to each other are the known joining methods of glueing or welding.

According to another embodiment, the piston member, frictional engagement element and elastic element are configured as a single, integral element.

An integral piston with an integral piston member, frictional engagement element and elastic element can be readily and immediately used without further assembly steps being necessary. Even if production of an integral piston may be more complex than the production of a separate piston member, frictional engagement element and elastic element, an integral configuration still allows simpler logistics because the piston does not have to be assembled or combined from separate parts in order to assemble the syringe.

In one preferred embodiment, the piston is produced in conjunction with the piston member, frictional engagement element and elastic element in a two- or multi-component injection moulding process.

The two- or multi-component injection moulding process, which is known per se, allows the production of integral components in which parts or sections have different properties, for example as a result of different materials. It is possible, for example, for a desired elasticity of the elastic member, a desired strength of the piston member and/or desired frictional characteristics of the frictional engagement element to be set independently of each other to a large extent, even when the piston is configured as an integral element. When state-of-the-art production technologies, such as two-component injection moulding, are used appropriately, it is possible for the region that includes the elastic element to consist of a relatively flexible material and for the adjacent region forming the piston member to consist of a relatively dimensionally stable material.

Another inventive alternative to the above consists in (only) the elastic element and the piston member being a single integral element. In this case, the frictional engagement element is configured as a separate element and is combined with the elastic element (and the piston member) when assembling the inventive syringe. As also in the case of the integral piston and also in the case of the integral frictionally engaging elastic element, the preferred production method is a two- or multi-component injection moulding process.

In one possible embodiment of the invention, the elastic element extends in a plane perpendicular to a longitudinal axis of the piston member around the piston member and engages with an outer surface of the piston member, in particular with the elastic element being anchored on said outer surface (see, for example, FIG. 1c, 2c, 2d, 9c, 13c or 15c).

One possible way of anchoring the elastic element on the piston member is to have the elastic element abut the outer surface of the piston member, with the elastic element extending substantially perpendicular to a longitudinal axis of the piston member. In this case, as described above, the frictional engagement element may be located between the elastic element and the inner wall of the sleeve, wherein a force acting transversely to a plane of the elastic element arises due to a relative movement between the frictional engagement element and the piston member, with which force the elastic element is tensioned.

In one advantageous embodiment of the invention, the elastic element is accommodated at least partially in a recess in the piston member (see, for example, FIG. 1c, 2c, 2d, 9c, 13c or 15c).

When the elastic element is accommodated at least partially in a recess in the piston member, a displacement of the elastic element along a longitudinal axis of the piston member can be easily prevented by this spatial arrangement, since the recess prevents such displacement by means of its outer limits. The piston member preferably has a recess, therefore, for at least partially accommodating the elastic element, wherein at least one delimitation of the recess prevents longitudinal displacement of the elastic element such that the elastic element is fixed in the axial direction inside the recess.

Figure 10A:
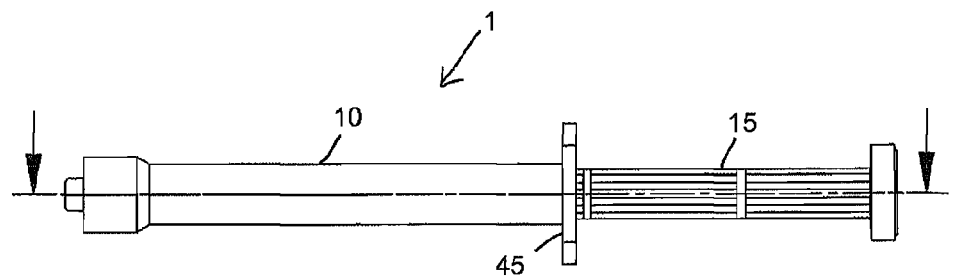
Figure 10B:
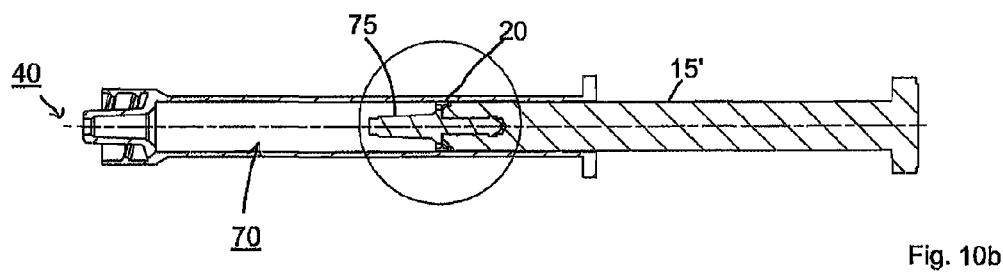
Figure 10C:
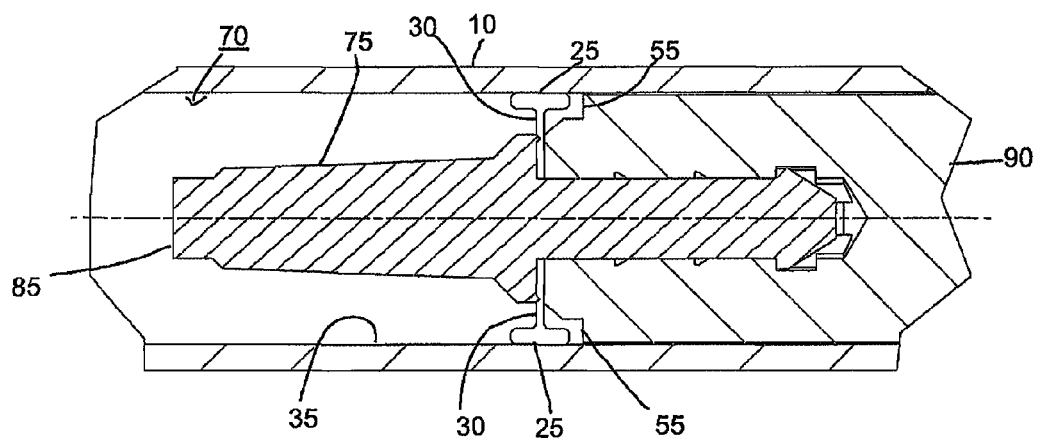

In yet another embodiment, the elastic element is tensioned inside the piston member, In particular between a first and a second portion of the piston member (see, for example, FIG. 10c).

Another possible way of anchoring the elastic element on the piston member is to fix it positively and/or force-lockingly by mounting the elastic element in the piston member. When the elastic element is suitably mounted in the piston member, assembly of the inventive piston and the inventive syringe is simpler than a method of assembly in which the elastic element is pulled onto a piston member and must be guided into a recess in the piston member. This configuration of the elastic element and piston member prevents unwanted detachment of the elastic member from the piston member, and particularly its withdrawal therefrom.

Figure 11:
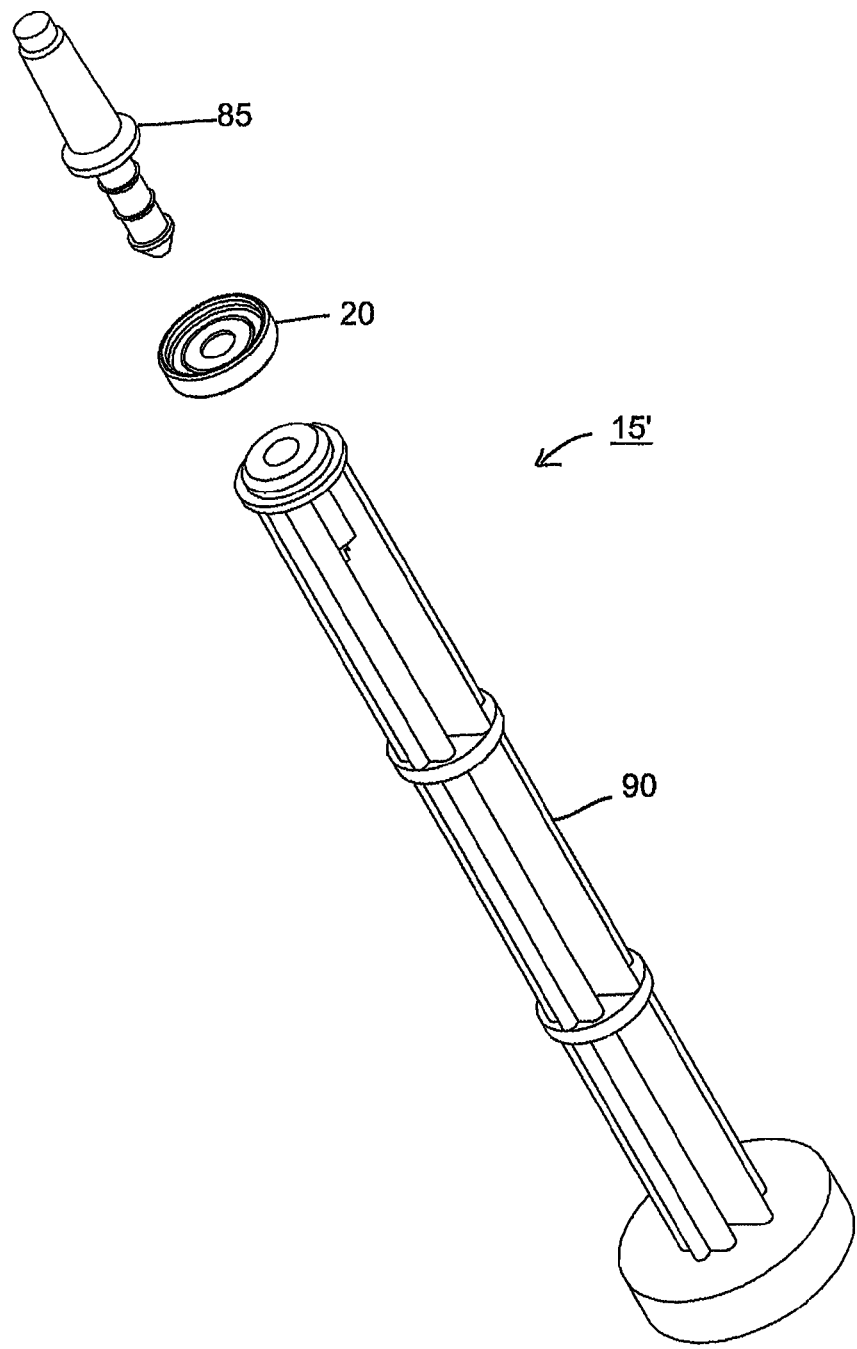

According to one preferred embodiment, the elastic element has an opening, in particular a central opening, through which the first portion of the piston member extends, wherein the first portion of the piston member and the second portion of the piston member are connected to each other (see, for example, FIG. 10c or 11).

Particularly when the elastic element is mounted between a first and a second portion of the piston member through an opening in the elastic element, it is possible for the elastic member to be mounted by means of a suitable connection between the first and second portion of the piston member. If the first and second portion of the piston member are connected with each other in such a way that a suitable fixing force is exerted on the elastic element, this results in the elastic element and the piston member being connected to each other force-lockingly. An alternative or addition to the above can consist in the elastic element being anchored by a force-locking connection by means of a suitable spatial configuration of the elastic element and the first and second portion of the piston member, or of the piston member in general.

In the above preferred embodiment, the first portion and the second portion of the piston member may be connected advantageously by means of a snap-fit and/or screw connection.

A snap-fit and/or screw connection of the first and second portion of the piston member permits simple mounting or anchoring of the elastic element on the piston member. In particular, it is not necessary, yet possible in this case that the connection between the first and second portion of the piston member can be non-destructively released. Other possible ways of forming the connection, including a welding and/or glued connection, are also conceivable.

Figure 5A:
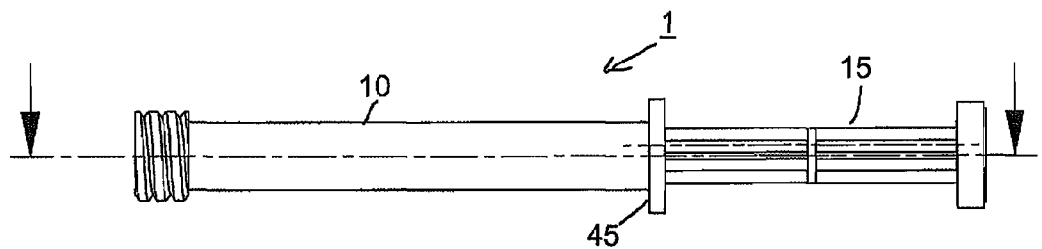
Figure 5B:
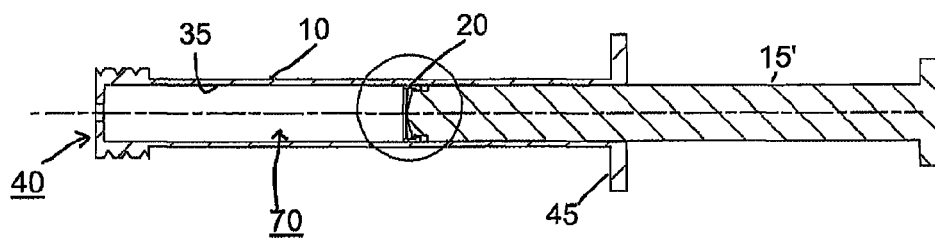
Figure 5C:
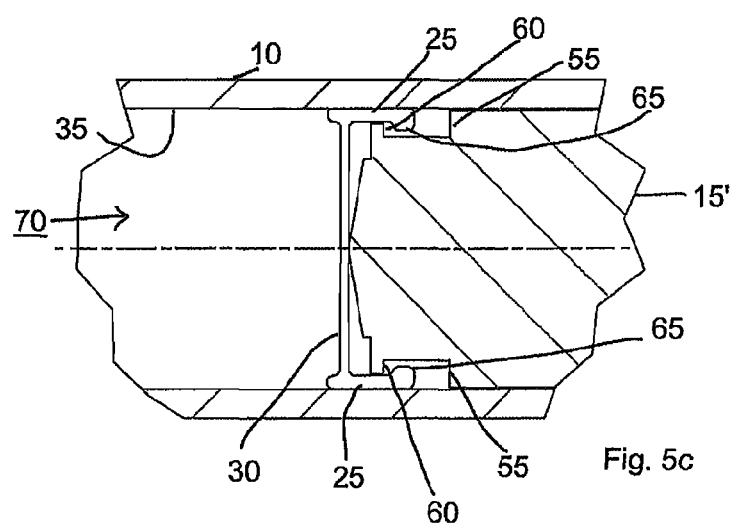
Figure 6A:
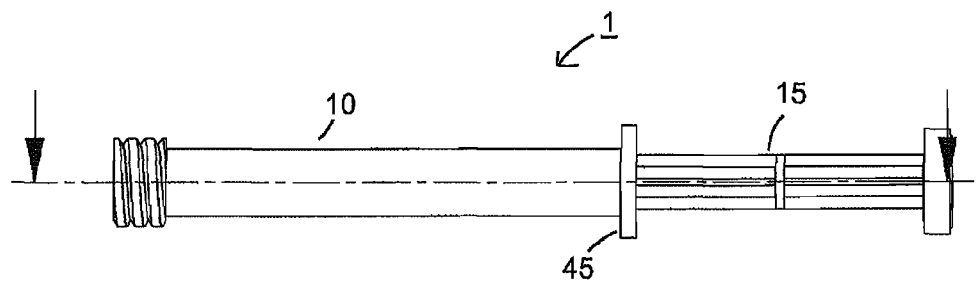
Figure 6B:
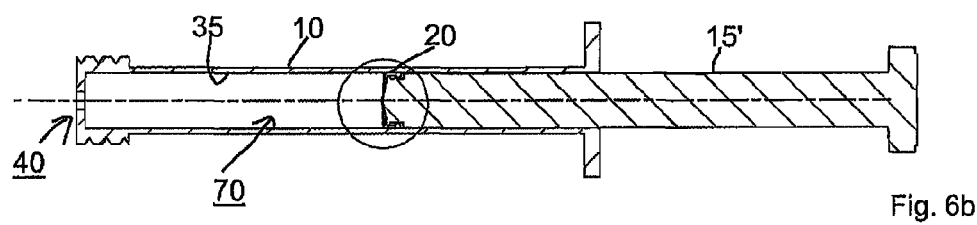
Figure 6C:
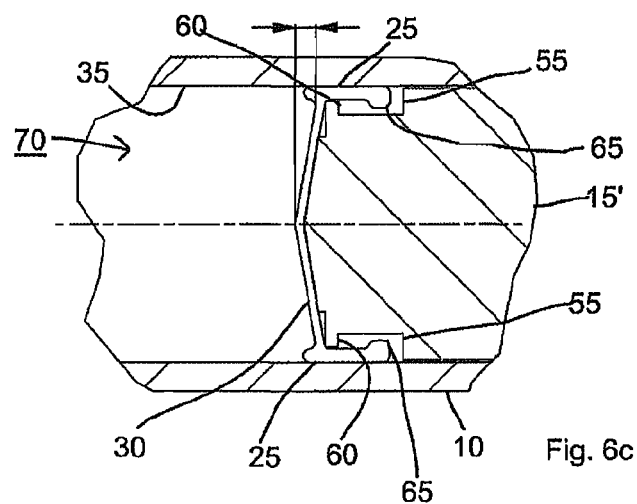
Figure 7A:
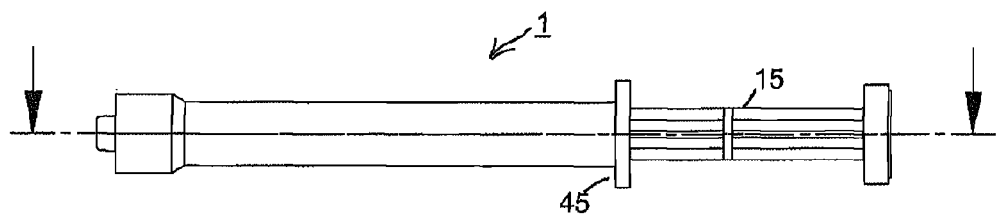
Figure 7B:
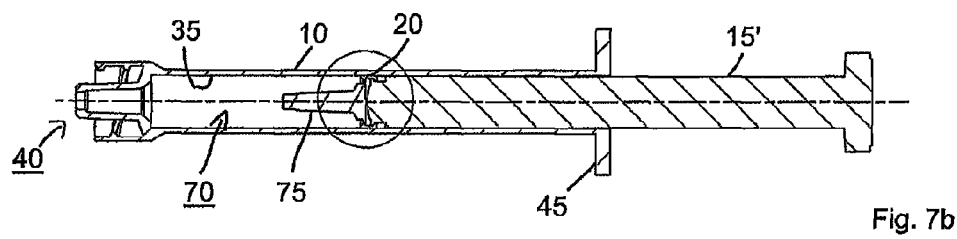
Figure 7C:
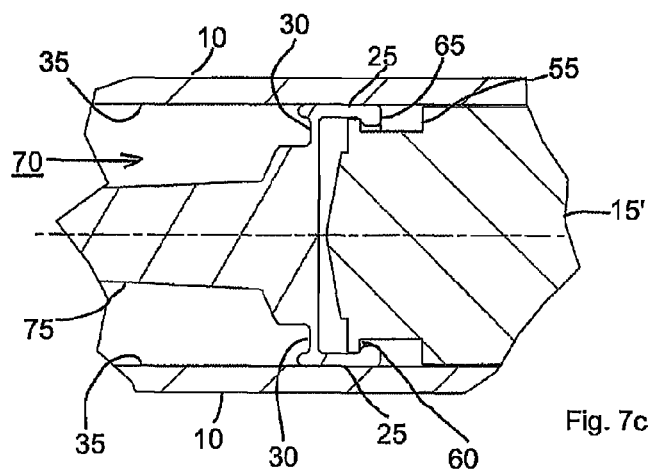

In one preferred embodiment of the invention, the elastic element and the frictional engagement element are disposed between the inner sleeve chamber and the piston member when the piston is inserted into the sleeve (see, for example, FIG. 5c, 6c or 7c).

Alternatively or additionally to anchoring the elastic element on the piston member, the elastic element (preferably also in combination with the frictional engagement element) may be provided in front of the piston member in the direction of insertion, so that insertion of the piston member into the sleeve causes the frictional engagement element to be displaced accordingly, and/or the elastic element to be tensioned to a desired degree.

According to one inventive embodiment, the sleeve has a tapering discharge opening, wherein the piston is provided with a tip that is adapted to the discharge opening.

In many cases, expulsion of material accommodated in the sleeve can be improved by means of a discharge opening that tapers or is smaller in relation to the sleeve cross-section; it is advantageous, especially when filling the syringe from the front, i.e. through the discharge opening, when the piston is provided with a suitable tip that fills the inner region of the discharge opening.

Figure 9A:
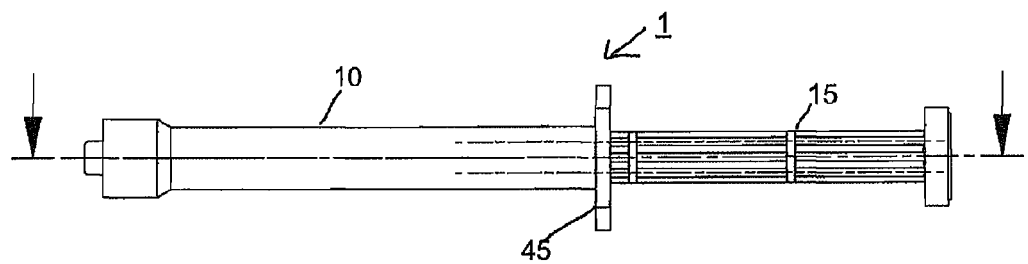
Figure 9B:
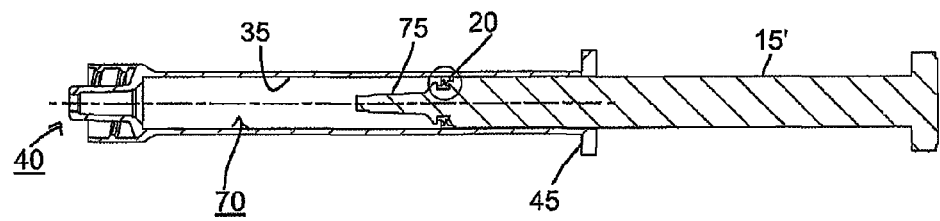
Figure 9C:
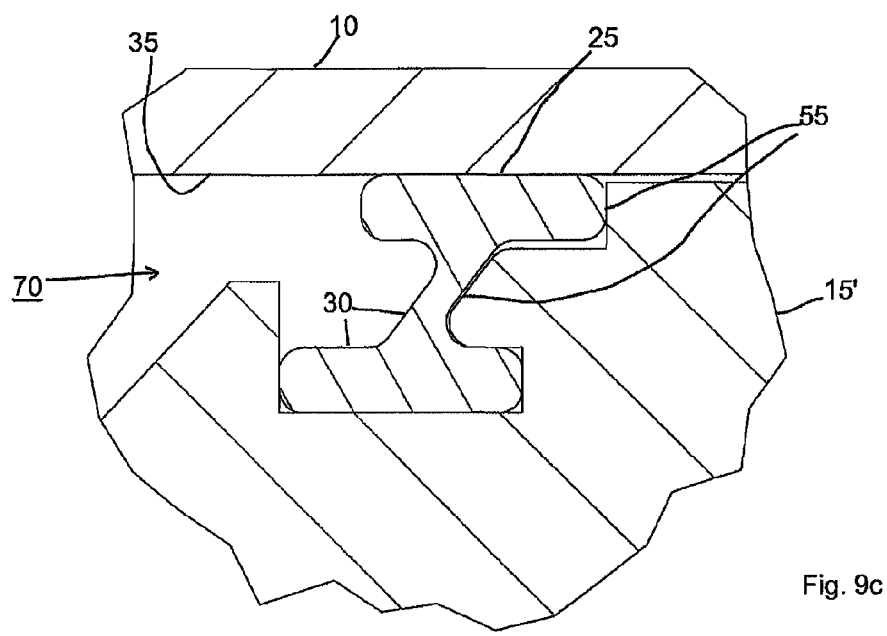

In another embodiment of the invention, a limiting means is provided for limiting relative movement between the frictional engagement element and the piston member to a predetermined distance from a relative starting position (see, for example, FIG. 6c, 7c or 9c).

The relative displacement between the frictional engagement element and the piston member is dependent on the force resulting from the deflection or tension of the elastic element. It is advantageous when only a predetermined maximum deflection of the elastic element is permitted, i.e. a limited relative movement between the frictional engagement element and the piston member, particularly so that the material of the elastic element is protected. Limiting the resultant tensile force on the elastic element can also ensure that the tensile force does not exceed the frictional force acting on the frictional engagement element, thus releasing the frictional engagement element in an undesired and possibly uncontrolled manner.

In one preferred embodiment of the invention, the syringe, in particular the piston member, has a first limiting element for limiting the relative movement between the frictional engagement element and the piston member on insertion of the piston into the sleeve, in particular a shoulder or edge against which the frictional engagement element and/or the elastic element can abut when the elastic element is tensioned.

When the piston and/or the piston member is pushed or inserted into the sleeve, this results in engagement or abutting of the frictional engagement element and/or the elastic element, preferably by providing a shoulder or edge on the piston member, thus limiting, in a simple manner, the relative movement between the piston member and the frictional engagement element.

In another preferred embodiment of the invention, the syringe, in particular the piston member, comprises a second limiting element for limiting relative movement during at least partial removal of the piston and/or of the piston member from the sleeve, wherein the piston member is provided in particular with a first protrusion which engages a second protrusion of the frictional engagement element and/or of the elastic element such that the first protrusion can abut the second protrusion on removal of the piston and/or of the piston member (see, for example, FIG. 5c, 6c, 7c).

When the piston member and the frictional engagement element are configured in such a way that removal of the frictional engagement element from the surroundings of the piston member when the piston member or piston is pulled out of the sleeve is prevented, it is also possible, for example, for the elastic element to be provided independently of fixation to the piston member, for example as a disc-shaped element between the piston member and the inner sleeve chamber. Due to the spatial engagement of the frictional engagement element and the piston member, a predetermined relative spatial arrangement of the frictional engagement element, the elastic element and the piston member to each other is also ensured, therefore, when the piston is being pulled out of the sleeve. Such removal is carried out, for example, when the sleeve is filled manually with material through the discharge opening.

In one advantageous embodiment of the invention, the elastic element can be tensioned by a shearing force, a tensile force and/or by a compressive force on insertion of the piston and/or the piston member.

Advantageously, the elastic element can be sheared, pulled or pressed with simple elastic elements in order to exert a force or to store energy in the elastic element. Other types of force exertion or storage are likewise possible.

According to yet another embodiment of the invention, the elastic element has at least one stiffening element, in particular a plurality of stiffening elements distributed evenly over the elastic element (see, for example, FIGS. 8a-d).

By providing one or a plurality of stiffening elements in the elastic element, it is possible to achieve desired tensile characteristics with greater independence from individual spatial configurations of the elastic element.

In another advantageous embodiment of the present invention, the sleeve is provided with a discharge opening having a projection for receiving a filling tube, wherein said projection tapers, in particular conically, from the outward periphery in the direction of the inner sleeve chamber. It is especially preferred that the projection tapers conically with an angle of 0.25-2° in relation to the middle axis, in particular at an angle of 0.5° (corresponding to a taper angle range from 0.5°-4°, or a taper angle of 1°).

The invention also relates to a piston for a syringe for dosed dispensing of material, in particular of free-flowing and/or pasty dental material, preferably for a syringe as described in the foregoing or for use in a method as described above, wherein the piston can be inserted into the sleeve and comprises a piston member, a frictional engagement element which can frictionally abut an inner wall of the sleeve, and an elastic element coupling the frictional engagement element and the piston member, wherein the piston is configured to define, with the sleeve, when the piston is inserted into the sleeve, an inner sleeve chamber for accommodating the material, wherein the elastic element can be tensioned on insertion of the piston and/or of the piston member into the sleeve by means of a relative lag of the frictional engagement element in relation to the piston member, wherein by relaxing the elastic element it is possible for the piston member to be expelled at least partially from the sleeve while the frictional engagement element remains motionless, in order to increase the volume of the inner sleeve chamber.

The invention also relates to a frictionally engaging elastic element for a syringe as described above, comprising a frictionally engaging element and an elastic element.

In one advantageous embodiment, the frictionally engaging elastic element according to the invention has a profile ring with a substantially H-shaped cross-section, wherein the outer profile limb forms the frictional engagement element, and the transverse profile limb and the inner profile limb form the elastic element, wherein the inner profile limb is configured to engage with an outer surface of a piston member (see, for example, FIG. 1c, 2c, 2d, 3b, 4b, 9c or 15c).

In a profile ring having a substantially H-shaped cross-section, a suitable support surface for the outer profile limb, i.e. for the frictional engagement element, results on an inner wall of the sleeve, the inner profile limb ensuring that the elastic element lies on an outer surface of the piston member, while the transverse profile limb of the cross-section permits, in particular, a shearing of the frictionally engaging elastic element in order to tension the elastic element.

In a preferred modification of the advantageous embodiment of substantially H-shaped cross-section as described above, the inner profile limb (as part of the elastic element) extends a lesser amount in the longitudinal direction of the syringe than the outer profile limb (as the frictional engagement element). When the outer profile limb is lengthened or enlarged in this manner, this produces the advantage that the sealing lip formed by the outer profile limb is pressed over a larger area against the inner sleeve chamber by the pressure in the medium resulting from application, in particular in the case of a narrow or very narrow needle, as a result of which an especially efficacious sealing effect can be achieved.

In another advantageous modification, the transverse profile limb of the frictionally engaging elastic element, which as part of the elastic element connects the inner profile limb and the outer profile limb, has a thickness in the longitudinal direction of the syringe that decreases in the outward radial direction.

In other words, in this modification the thickness of the transverse profile limb between the inner profile limb and the outer profile limb increases from the outside to the inside, wherein the term "thickness" relates here to the distance between the peripheral surface of the transverse profile limb facing the inner sleeve chamber and the peripheral surface of the transverse profile limb facing away from the inner sleeve chamber. Such outward tapering of the transverse profile limb allows a desired reduction in the restoring force to be achieved; such reduction may be desirable, depending on the viscosity of the material to be dispensed, but without a very thin transverse profile limb having to be produced. When a relatively large proportion of a transverse profile limb has a small cross-section, this can increase the risk of production errors, in the form of incorrect filling, especially when produced in an injection-moulding process.

In an alternative advantageous embodiment of the present invention, the frictionally engaging elastic element includes a profile ring having a substantially T-shaped cross-section, wherein the outer profile limb (corresponding to the horizontal stroke in the letter "T") forms the frictional engagement element, and the transverse profile limb (corresponding to the vertical stroke in the letter "T") forms the elastic element, the elastic element being configured to be mounted in a piston member (see, for example, FIG. 10c). Another alternative consists in a substantially L-shaped cross-section, wherein the transverse profile limb of the L-shaped cross-section abuts one end of the outer profile limb and not, as with the T-shaped cross-section, at the middle section of the outer profile limb.

If the frictionally engaging elastic element is embodied in the shape of a profile ring with a substantially T-shaped cross-section, this frictional engagement element has a middle opening through which a first or a second portion of the piston member can extend for fixing or anchoring the frictionally engaging elastic element, wherein the frictionally engaging elastic element can be held both force-lockingly and positively by virtue of the first and second portion of the piston member being connected to each other. The transverse profile limb, in particular, forms the elastic element, which can be mounted in a simple manner and is exposed to a shearing or bending force when the elastic element is tensioned.

The outer profile limb of the frictionally engaging elastic element then assumes the function of the frictional engagement element.

In yet another alternative embodiment, the frictionally engaging elastic element according to the invention includes a substantially saucer-shaped region, the edge of the saucer-shaped region forming the frictional engagement element and the middle portion of the saucer-shaped region forming the elastic element (see, for example, FIG. 5c, 6c or 7c).

The frictionally engaging elastic element may also be saucer- or disc-shaped, the outer region or edge of the frictionally engaging elastic element performing the function of the frictional engagement element, i.e. engagement with the inner wall of a sleeve and creation of frictional engagement, thus achieving tensioning of the elastic element by deformation of the inner or middle region of the saucer- or disc-shaped frictionally engaging elastic element.

According to one advantageous embodiment of the invention, the frictional engagement element of the frictionally engaging elastic element preferably has a protrusion which is configured for engagement in a recess of a piston member.

If the frictional engagement element of the frictionally engaging elastic element is provided with a protrusion which can engage with a recess in the piston member, it is possible in this way to fix the piston member and frictionally engaging elastic element relative to each other, wherein the size or configuration of the recess nevertheless permits relative movement between the frictional engagement element and the piston member at least.

In the above references to the enclosed Figures, each of the Figures is intended only to illustrate individual aspects by way of example. The Figures are not to be understood as restrictions or limitations of the invention. The above references are intended purely as an aid to understanding.

Figure 13A:
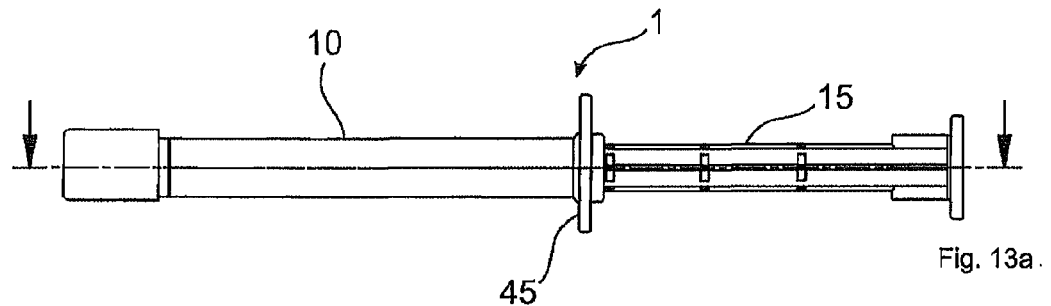
Figure 13B:
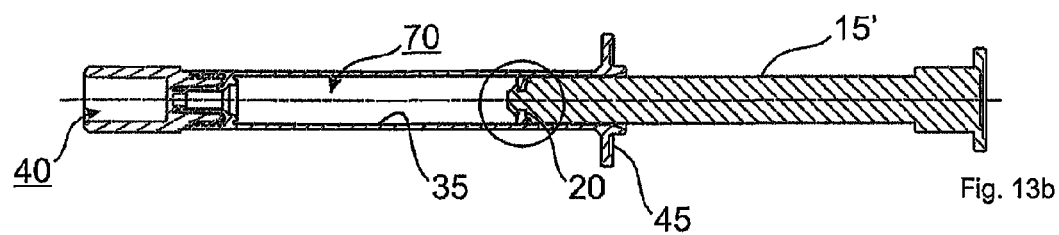
Figure 13C:
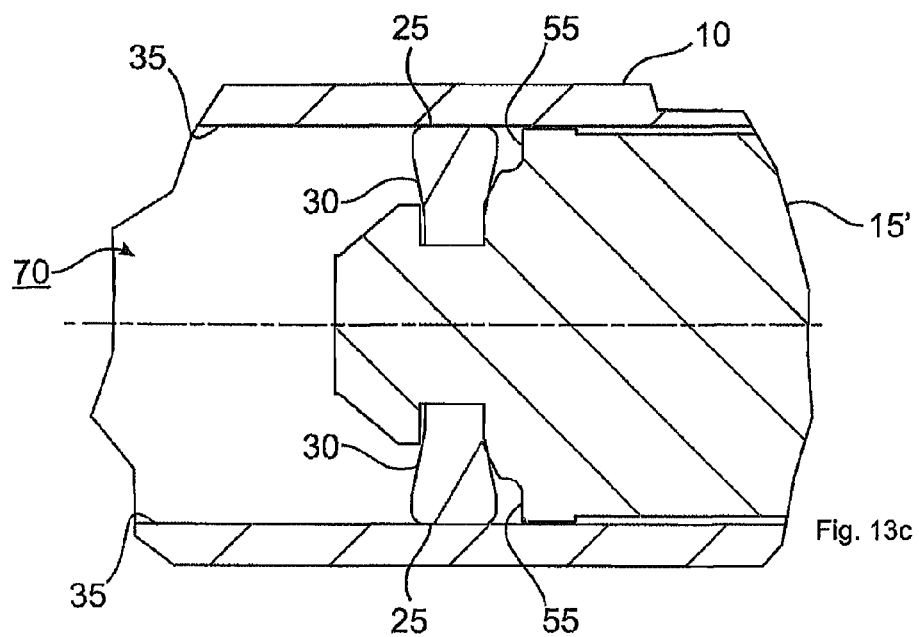
Figure 14:
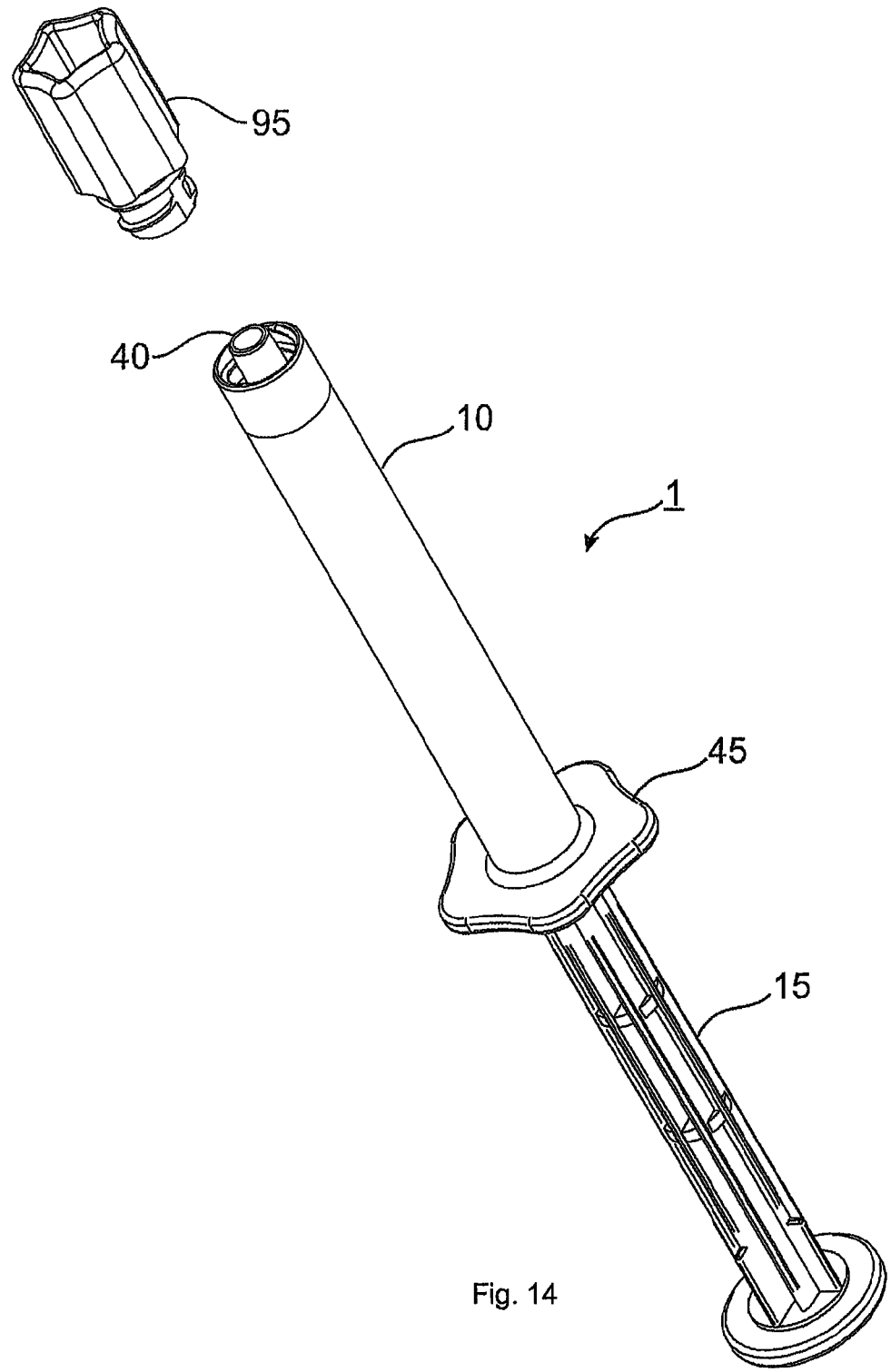
Figure 15A:
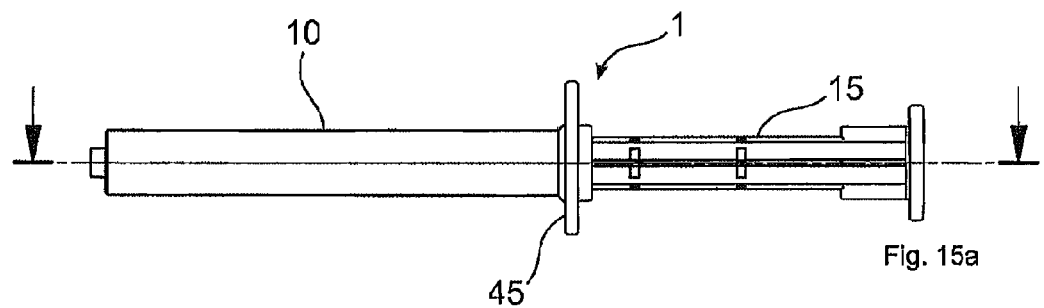
Figure 15B:
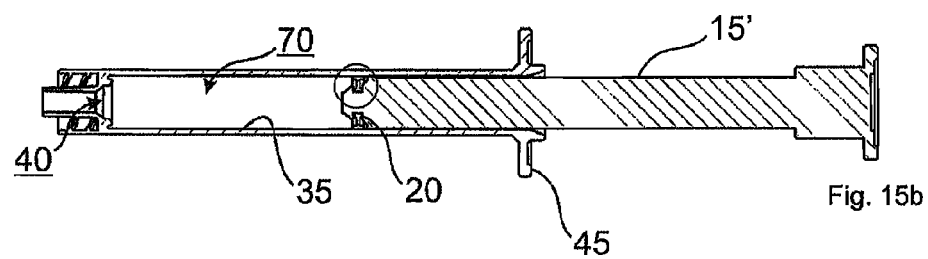
Figure 15C:
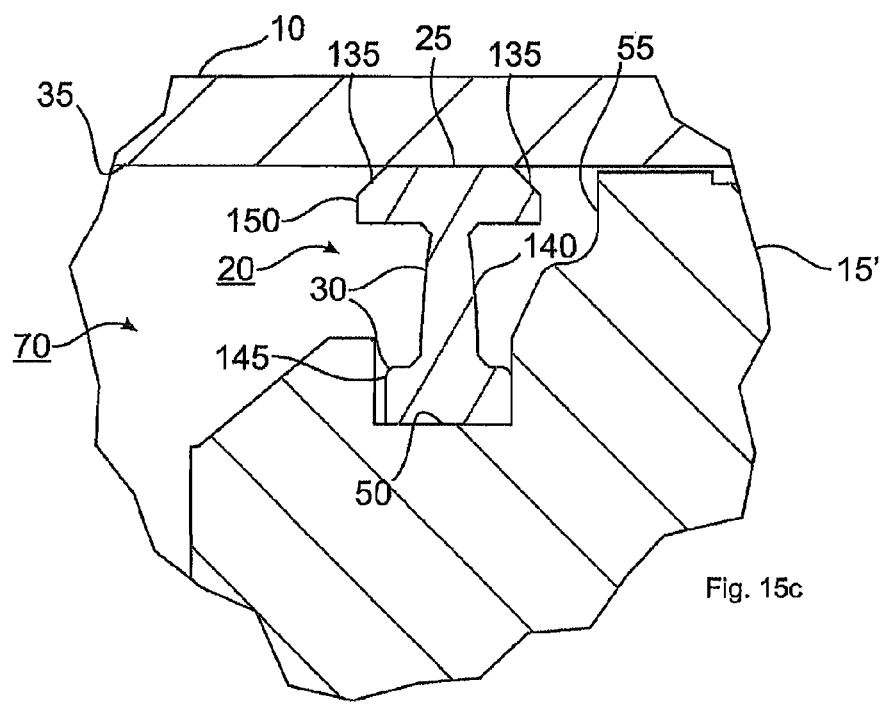
Figure 16A:
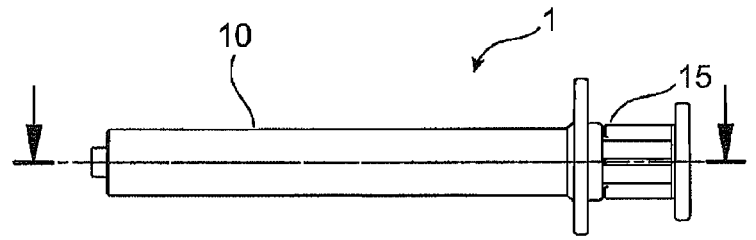
Figure 16B:
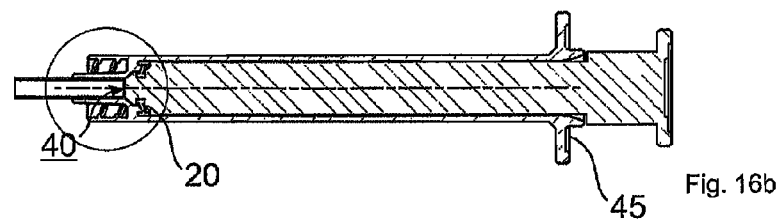
Figure 16C:
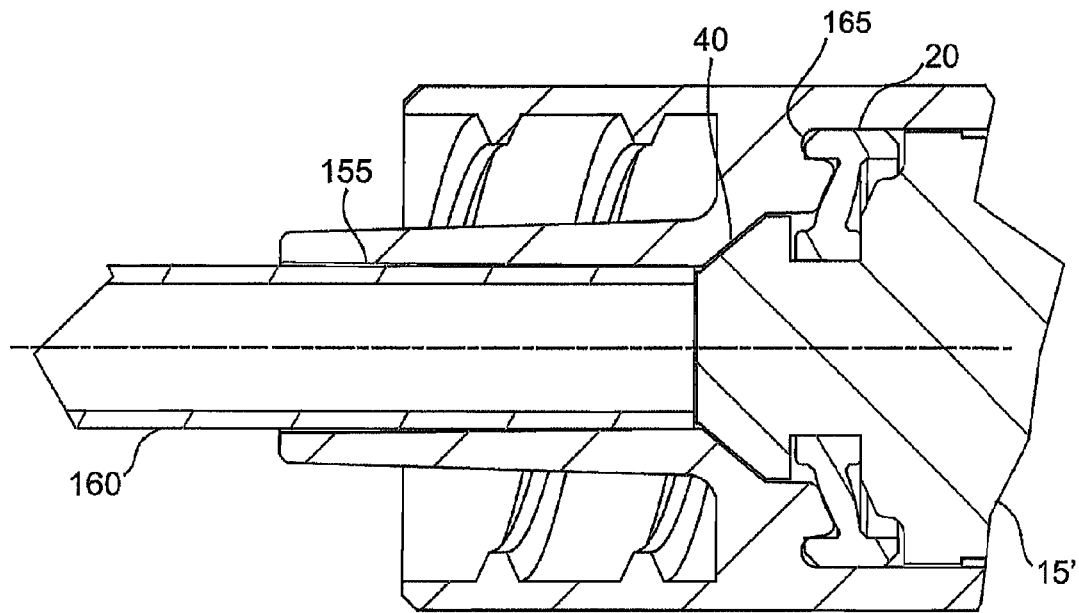

In the following, the invention shall be described in greater detail with reference to preferred embodiments and to the enclosed Figures, in which FIGS. 1a, 1b and 1c respectively show a first embodiment of a syringe according to the invention in a side view, in cross-section and in a sectional enlargement, in a state in which the elastic element is untensioned, FIGS. 2a, 2b, 2c, 2d respectively show the first embodiment of the inventive syringe in FIGS. 1a, 1b and 1c, in a side view, in cross-section, in a sectional enlargement and in a further enlargement, in a state in which the elastic element is tensioned, FIGS. 3a, 3b respectively show a plan view and a cross-sectional view of a first embodiment of a frictionally engaging elastic element according to the invention, similar to the first embodiment of the inventive syringe in the untensioned state, FIGS. 4a, 4b respectively show a plan view and a cross-sectional view of the first embodiment of a frictionally engaging elastic element according to the invention as shown in FIGS. 3a and 3b, in the tensioned state, FIGS. 5a, 5b, 5c respectively show a second embodiment of a syringe according to the invention, in a side view, in cross-section and in a sectional enlargement, in a state in which the elastic element is untensioned, FIGS. 6a, 6b, 6c respectively show the second embodiment of the inventive syringe in FIGS. 5a, 5b and 5c, in a side view, in cross-section and in a sectional enlargement, in a state in which the elastic element is tensioned, FIGS. 7a, 7b, 7c respectively show a third embodiment of a syringe according to the invention, in a side view, in cross-section and in a sectional enlargement, in a state in which the elastic element is untensioned, FIGS. 8a, 8b, 8c, 8d respectively show a second embodiment of a frictionally engaging elastic element according to the invention, in a schematic view, a first cross-section, a second cross-section and in perspective view, FIGS. 9a, 9b, 9c respectively show a fourth embodiment of a syringe according to the invention, in a side view, in cross-section and in a sectional enlargement, in a state in which the elastic element is tensioned, FIGS. 10a, 10b, 10c respectively show a fifth embodiment of a syringe according to the invention, in a side view, in cross-section and in a sectional enlargement, in a state in which the elastic element is untensioned, FIG. 11 shows an exploded perspective view of an embodiment of a piston according to the invention, as provided in the embodiment of a syringe shown in FIGS. 10a, 10b and 10c, FIG. 12 shows a schematic flow diagram of an embodiment of a method according to the invention, FIGS. 13a, 13b, 13c respectively show a sixth embodiment of a syringe according to the invention, in a side view, in cross-section and in a sectional enlargement, in a state in which the elastic element is untensioned, FIG. 14 shows a perspective view of one embodiment of a syringe according to the invention;

FIGS. 15a, 15b, 15c respectively show a seventh embodiment of a syringe according to the invention in a side view, in cross-section and in a sectional enlargement, in a state in which the elastic element is untensioned, and FIGS. 16a, 16b, 16c respectively show a seventh embodiment of a syringe according to the invention, in a side view, in cross-section and in a sectional enlargement, in a state in which the elastic element is tensioned.

Similar or corresponding elements are marked in the Figures with the same reference signs, even when the elements are configured differently in different embodiments.

Figure 1B:
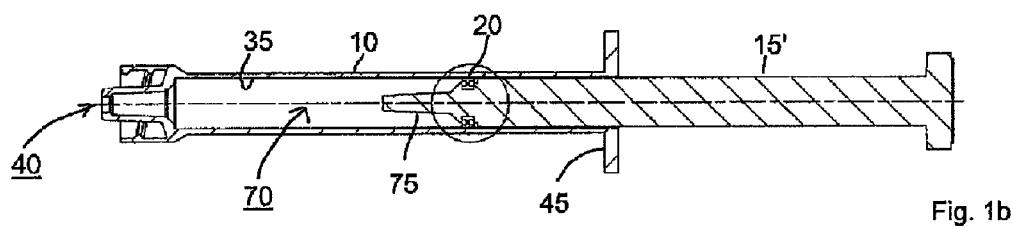
Figure 1C:
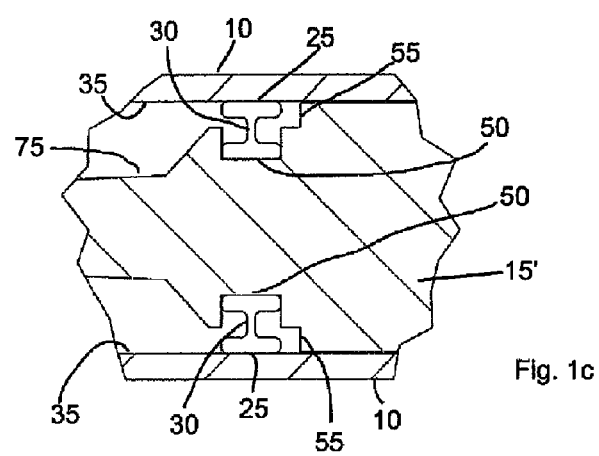

FIGS. 1a, 1b, 1c respectively show a first embodiment of a syringe according to the invention in a side view, in cross-section and in a sectional enlargement, in a state in which the elastic element is untensioned. FIG. 1a shows an inventive syringe according to a first embodiment, in a no-load position. FIG. 1b is a cross-section along the line shown. FIG. 1c shows the sealing region and the region around the frictionally engaging elastic element, in an enlarged view.

FIG. 1a shows syringe 1 according to the first embodiment of the invention. Syringe 1 comprises a sleeve 10 and a piston 15, of which only the member can be seen in FIG. 1. At the end opposite its discharge opening, sleeve 10 has a grip 45 which facilitates operation of syringe 1 when pressing in piston 15. The end opposite the discharge opening is used to receive piston 15.

In FIG. 1b, syringe 1 is shown in a cross-sectional view. Syringe 1 has sleeve 10 comprising an inner wall 35, a discharge opening 40 and grip 45. The piston comprising piston member 15' and the frictionally engaging elastic element 20, an integral combination comprising a frictional engagement element and an elastic element, is inserted into sleeve 10. Piston member 15' has a tip 75 which is spatially adapted to discharge opening 40. Sleeve 10 encloses an inner sleeve chamber 70 which is defined on one side opposite discharge opening 40 by the piston, that is, by piston member 15' (or tip 75) and by the frictionally engaging elastic element.

FIG. 1c shows an enlarged view of the region around the frictionally engaging elastic element 20 shown in FIG. 1b. The frictionally engaging elastic element 20 is formed by an annular profile (shown here in cross-section only) which comprises an elastic element 30 and a frictional engagement element 25, wherein said frictionally engaging elastic element 20 has an H-shaped cross-section.

Frictional engagement element 25 frictionally abuts the inner wall 35 of sleeve 10, thus forming a seal against the passage of material out of inner sleeve chamber 70 and between the frictional engagement element 25 and inner wall 35.

Elastic element 30, which is formed by the transverse limb and inner limb of the profile ring, is accommodated in a recess 50 of piston member 15', said recess being adapted to accommodate abuttingly the inner limb of the profile ring, thus effecting a seal between the profile ring and the recess.

In FIGS. 1a, 1b and 1c, elastic element 30 is shown in the untensioned state.

Figure 2A:
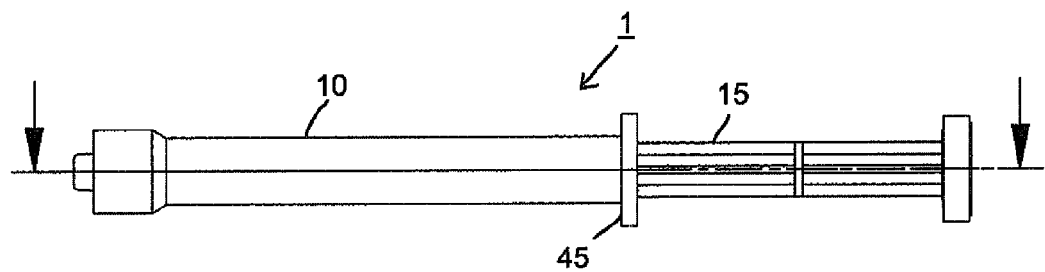
Figure 2B:
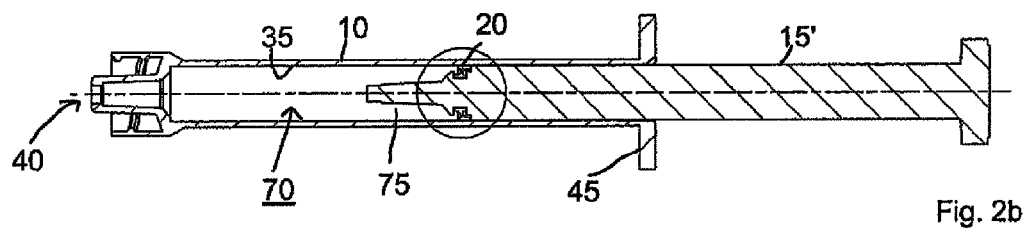
Figure 2C:
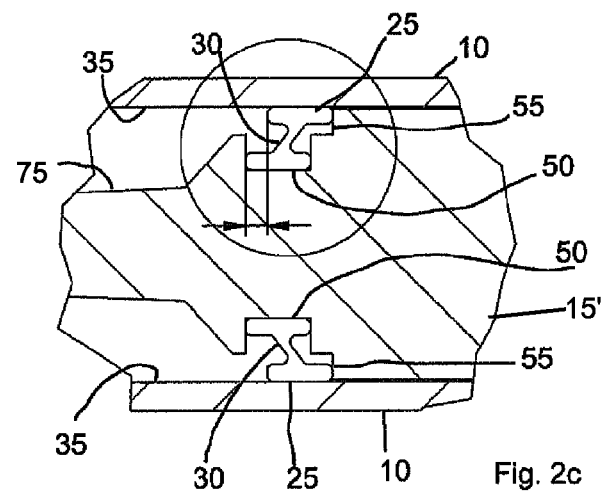
Figure 2D:
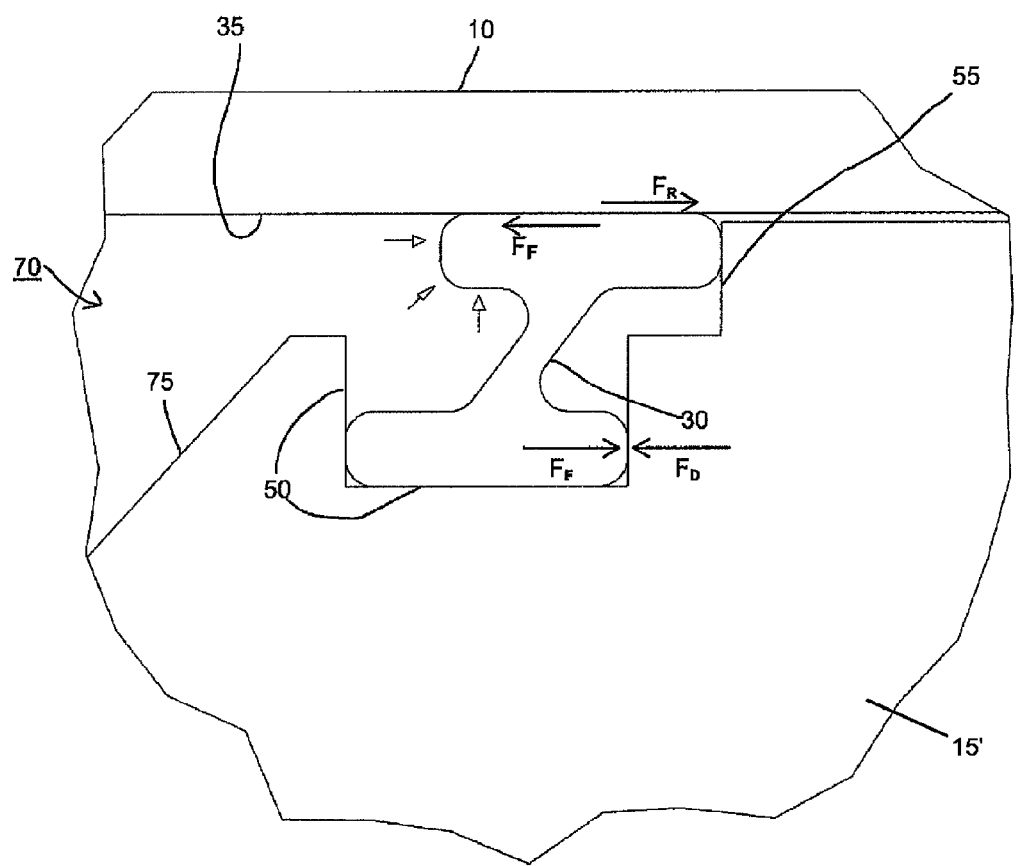

FIGS. 2a, 2b, 2c, 2d respectively show the first embodiment of the inventive syringe in FIGS. 1a, 1b and 1c, in a side view, in cross-section, in a sectional enlargement and in a further enlargement, in a state in which the elastic element is tensioned. FIG. 2a shows the syringe of FIGS. 1a, 1b and 1c in a position during dispensing of material, i.e. with a tensioned elastic element. In the cross-section shown in FIG. 2b, and even better in the enlargement of the sealing region in FIG. 2c, it can be seen how the elastic element 30 of the seal or of the frictionally engaging elastic element 20 has elastically deformed. A more enlarged view of one side of the seal is depicted in FIG. 2d.

FIGS. 2a and 2b largely correspond to the view of the first embodiment shown in FIGS. 1a and 1b. The difference is that elastic element 30 is tensioned in the former case.

It can be seen more clearly in FIG. 2c that elastic element 30 is tensioned by the action of a shearing force, wherein an offset arises between the inner limb and the outer limb of the profile ring. This shearing or tensioning is effected by inserting the piston (member) into the sleeve, in the process of which the frictional engagement element 25 does not completely follow the insertion of piston member 15', due to the frictional force which acts upon said element. Since elastic element 30 is firmly anchored to piston member 15', with its inner profile limb inside recess 50, a relative movement occurs between frictional engagement element 25 and the inner profile limb (and piston member 15'). This relative movement results in tensioning of elastic element 30.

In FIG. 2c, it can also be seen that the frictional engagement element 25 abuts an edge 55 of piston member 15'. If piston member 15' or piston 15 continues to move into sleeve 10 (to the left in the Figures), further tensioning of the elastic element, in which larger spring forces would occur, is prevented by frictional engagement element 25 being carried forward by edge 55. Deformation of the frictionally engaging elastic element is limited by edge 55. In this way, it is possible, in particular, to prevent the frictionally engaging elastic element being overstretched or even torn.

As can be seen from FIG. 2d, in particular, frictional engagement element 30 has a lip which projects in the direction of the inner sleeve chamber 70. As indicated by the small arrows in FIG. 2d, a pressure is exerted on this lip by the material located in inner sleeve chamber 70, thus improving the sealing effect of frictional engagement element 30. A seal against the inner casing surface of the syringe body, i.e. against the inner wall 35 of sleeve 10, is supported by the lip-shaped circumferential edge of frictional engagement element 25, against which a fluid pressure is exerted by a liquid or free-flowing material.

Force arrows, symbolizing in simplified form the forces acting, are also shown in FIG. 2d. A compressive force $F_D$ acts initially from piston member 15' on the tensioned elastic element 30. The tensioned elastic element exerts a force $F_F$ on piston member 15'. In the state of equilibrium considered here, the forces are equal. However, the force $F_F$ of elastic element 30 also acts on frictional engagement element 25 and via frictional engagement element 25 on the boundary to inner wall 35. The opposite frictional force $F_R$ to this spring force $F_F$ also acts between inner wall 35 and frictional engagement element 25. In the case under consideration, the frictional force $F_R$ is equal to the spring force $F_F$.

It is irrelevant for the present equilibrium case whether the piston is currently being inserted into the sleeve or whether the piston is motionless relative to the sleeve. However, one difference between insertion and motionlessness is the size of the frictional force, that is, there may be a difference between the static friction and the sliding friction between inner wall 35 and frictional engagement element 25.

The equilibrium of forces leads (within certain limits that are defined here by edge 55, inter alia) to a certain orientation of the elements with respect to each other. If the compressive force acting is greater than the force $F_D$ shown, this would lead—as long as there is no abutting of the frictional engagement element against edge 55—to a greater tension or deformation of elastic element 30, which in turn would have a corresponding effect on the balance of forces at the boundary between inner wall 35 and frictional engagement element 25. As long as spring force $F_F$ is less than or equal to frictional force $F_R$, the deflection and tensioning caused by the frictional force is maintained and increased, respectively. If the spring force is greater than the frictional force (in the case of a transition from static friction to sliding friction, for example), the deformation of elastic element 30 will be restored until the (decreasing) spring force and the frictional force are returned to equilibrium. Any displacement between frictional engagement element 25 and (the inner limb of) elastic element 30, or change in the tension in elastic element 30, is limited by edge 55. As soon as frictional engagement element 25 abuts edge 55, force is directed into frictional engagement element 25 via edge 55 directly, and no longer via elastic element 30 only, with the result that the frictional force can also be overcome when the spring force alone is not sufficient for this purpose. In other words, the generation of a spring force is limited to a certain maximum value because edge 55 (and piston member 15') causes force to be exerted on the frictionally engaging elastic element as a whole as soon as there is abutment, and no longer just on elastic element 30, with the result that no further deformation or tensioning of the frictionally engaging elastic element occurs.

FIGS. 3a, 3b respectively show a plan view and a cross-sectional view of a first embodiment of a frictionally engaging elastic element according to the invention, similar to the first embodiment of the inventive syringe in the untensioned state.

FIG. 3a and FIG. 3b show a frictionally engaging elastic element 20 according to the invention, which can also be used as a seal, in a no-load, i.e. untensioned state. The frictionally engaging elastic element 20 consists of an integral profile ring of H-shaped cross-section. The outer limb of the H forms frictional engagement element 25, whereas the inner limb and the transverse limb together form elastic element 30. The frictionally engaging elastic element 20 has a symmetrical shape. This facilitates assembly, i.e. the assembly of the inventive syringe. The front and rear side are configured identically, as a result of which the frictionally engaging elastic element 20 can be placed on the piston member regardless of orientation. Such a configuration eliminates a source of error that might otherwise result in incorrect assembly due to wrong orientation.

FIGS. 4a, 4b respectively show a plan view and a cross-sectional view of the first embodiment of a frictionally engaging elastic element according to the invention as shown in FIGS. 3a and 3b, in the tensioned state. The frictionally engaging elastic element 20 is in a deformed state in which the frictional engagement element 25 is displaced in relation to its resting state, and in particular in relation to the inner limb of elastic element 30, along an axis perpendicular to the plane of the frictionally engaging elastic element 20. As a consequence of this displacement and deformation, elastic element 30 is placed under tension, wherein the frictionally engaging elastic element 20 exerts a force in order to return to the untensioned resting state. In the mounted state, these forces are absorbed, on the one hand, via the friction between the frictional engagement element 25 and the inner wall of a sleeve against which the frictional engagement element 25 abuts, and, on the other hand, are transferred to the piston member to which the frictional engagement element 20 is attached, in particular via the inner limb. The frictionally engaging elastic element 20 is deformed into its tensioned state, as shown, on the one hand by the action of a force by the piston member, acting parallel to the middle axis of the frictionally engaging elastic element 20, and on the other hand by friction at the inner wall.

FIGS. 5a, 5b, 5c respectively show a second embodiment of a syringe according to the invention, in a side view, in cross-section and in a sectional enlargement, in a state in which the elastic element is untensioned.

Syringe 1 differs from the syringe shown in FIGS. 1a and 2a, firstly in the connection option at the discharge opening, where an external thread is shown here, in contrast to an internal thread. A needle, for example, is attached in this case using the external thread, or in a different manner in the case of other embodiments. Options include a bayonet connection or a cone with self-inhibition.

The discharge opening 40 is also substantially flat in shape. The main difference between the syringe according to the first embodiment and syringe 1 according to the second embodiment lies in the configuration of frictional engagement element 20 and of piston member 15'; the first and second embodiments are otherwise identical.

The frictional engagement element 20 has a substantially flat surface on its side facing inner sleeve chamber 70, said surface being formed by a disc-shaped elastic element 30. Frictional engagement element 25 abuts the outer side of elastic element 30 such that elastic element 30 and inner wall 35 of sleeve 10 are spaced apart from each other. Frictional engagement element 30 frictionally abuts inner wall 35 and extends substantially away from inner sleeve chamber 35, which is defined by piston 15 and sleeve 10. The frictional engagement element 35 has a protrusion 65 which extends inwards away from inner wall 35.

Piston member 15' has an obtuse tip at its front end facing inner sleeve chamber 70; the function of said tip is described further below with reference to FIGS. 6a, 6b and 6c. Piston member 15' has a circumferential, outwardly oriented (i.e. in the direction of the inner sleeve wall 35) protrusion 60 in its front region. As in the first embodiment, the piston member also has an edge 55, thus resulting in a recess in piston member 15' between edge 55 and the protrusion, into which recess the protrusion 65 of frictional engagement element 25 or of frictionally engaging elastic element 20 extends. Protrusion 65 of frictional engagement element 25, and hence the frictional engagement element itself, is fixed by protrusion 60 and edge 55 of piston member 15', in interaction with the inner sleeve wall 35, wherein the size (i.e. the extension) of the recess (in the longitudinal direction) determines an amount of play for frictional engagement element 25, within which movement relative to piston member 15' is possible, despite said fixing. The range of possible movement results either from the distance between edge 55 and protrusion 65 (with a correspondingly large or long frictional engagement element) or from the distance of protrusion 65 from where elastic element 30 joins frictional engagement element 25, as shown in FIG. 5c (see also FIG. 6c).

According to the second embodiment, the frictionally engaging elastic element 20 is continuous and separates piston member 15' from the inner sleeve chamber. The material contained in the syringe can be completely dispensed by means of an approximately flat piston member having an obtuse tip, if the discharge opening 40 of the syringe is short or flat. When filling the syringe, there is also very little or no trapping of air inside the syringe.

Due to the engagement of protrusions 60 and 65 of piston member 15' and of frictional engagement element 25, it is also possible for piston 15 to be pulled back, without releasing the frictionally engaging elastic element 20 from piston member 15'. Such withdrawal may be envisaged, in particular, for filling syringe 1 through the discharge opening, such withdrawal producing an underpressure in inner sleeve chamber 70 in order to suck in material in the form of a liquid, for example.

Compared to the way in which the frictionally engaging elastic element 20 is mounted on piston member 15 (i.e. into recess 50) when assembling the first embodiment, the second embodiment has the advantage of simpler assembly by placing the frictional engagement element 20 onto the tip of piston member 15'.

However, due to the asymmetry of frictionally engaging elastic element 20, it is necessary in the case of the embodiment shown that said element is positioned with the correct orientation.

FIGS. 6a, 6b. 6c respectively show the second embodiment of the inventive syringe in FIGS. 5a, 5b and 5c, in a side view, in cross-section and in a sectional enlargement, in a state in which the elastic element is tensioned.

As can be seen from FIG. 6c, especially, the elastic element 30 is in the tensioned state here. Elastic element 30 abuts the tip of piston member 15' due to the relative lag of frictional engagement element 25. Said tip is shaped like a very flat cone, so that elastic element 30 is not deformed too strongly. It can also be seen from FIG. 6c that frictional engagement element 25 does not abut the edge 55 of piston member 15' even when elastic element 30 is lying against the tip. The deformation and hence the tension of elastic element 30 is therefore determined in this case by the shape of the tip of piston member 15'.

FIGS. 7a, 7b, 7c respectively show a third embodiment of a syringe according to the invention, in a side view, in cross-section and in a sectional enlargement, in a state in which the elastic element is untensioned.

The third embodiment differs from the second embodiment in that—similar to the tip 75 of the piston member in the first embodiment—the frictionally engaging elastic element 20 is provided here with a tip 75 which is adapted to the tapering discharge opening 40 that is likewise provided. As an alternative to the integral embodiment shown, the tip may also be suitably attached to a frictional engagement element similar to that in the second embodiment. The above description of the second embodiment applies accordingly to the third embodiment as well.

FIGS. 8a, 8b, 8c, 8d respectively show a second embodiment of a frictionally engaging elastic element according to the invention, in a schematic view, a first cross-section, a second cross-section and in perspective view.

FIG. 8a shows a schematic view of a frictionally engaging elastic element 20 according to the second embodiment, in which the frictionally engaging elastic element 20 is provided with six stiffening elements 80. These of these stiffening elements are located on each opposite side of the frictionally engaging elastic element, as indicated in FIG. 8*a* by broken lines. FIGS. 8*b* and 8*c* respectively show cross-sectional views of frictionally engaging elastic element 20. Aside from the web-shaped stiffening elements or reinforcements 80, the frictionally engaging elastic element 20 is the same as the one in the first embodiment. The frictionally engaging elastic element 20 is equipped with the additional web-shaped reinforcements 80 in order to support its elastic properties. These webs may be located on one or preferably on both sides, and may be offset from each other in the manner shown. Their number may range from one to several.

FIGS. 9*a*, 9*b*, 9*c* respectively show a fourth embodiment of a syringe according to the invention, in a side view, in cross-section and in a sectional enlargement, in a state in which the elastic element is tensioned.

This fourth embodiment largely corresponds to the first embodiment, so a description of identical features can be dispensed with here. Unlike in the first embodiment of the syringe, piston member 15' according to the fourth embodiment is provided with an edge 55 against which the frictionally engaging elastic element 20 abuts both with its frictional engagement element 25 (as in the first embodiment) and which its deformed, i.e. tensioned, elastic element 30 in the tensioned state. The contour of edge 55 is configured in such a way that edge 55 supports the frictionally engaging elastic element 20 in the tensioned state across its entire surface, on the side of the frictionally engaging elastic element 20 facing away from inner sleeve chamber 70. By this means, deformation of the frictionally engaging elastic element is reliably limited across its entire extension, so the risk of damage, for example of tearing by incisions, is largely eliminated. According to the invention, however, intermediate forms between the configuration according to the first and fourth embodiment may also be provided in respect of edge or shoulder 55. By adapting edge 55 to the shape of the frictionally engaging elastic element, an undercut is provided in the fourth embodiment that provides an additional holding effect for the base part of the elastic element (inner limb of the H-shaped profile) that faces away from the inner sleeve chamber.

FIGS. 10*a*, 10*b*, 10*c* respectively show a fifth embodiment of a syringe according to the invention, in a side view, in cross-section and in a sectional enlargement, in a state in which the elastic element is untensioned.

What is shown is an embodiment according to the invention in which the frictionally engaging elastic element 20 is fixed, as a seal provided with a separate head piece 85 as the first portion of piston member 15', to a second portion 90 of piston member 15'. The head piece 85, for its part, is geometrically adapted to the discharge opening 40 in order to minimise as far as possible the presence of air in the front side of syringe 1. By means of such adaptation, syringe 1 can be filled from the front end in a largely airless manner.

Head piece 85 is connected to the second portion 90 of piston member 15' by a press fit. A thickening in the form of a snap-fit connection provides additional protection against undesired separation from the first and second portions 80, 90 of the piston member. Other thickenings in the form of barbs are also present, which do not engage at the end, but which likewise prevent removal due to the elasticity of the plastic of the second portion 90 of piston member 15'. It is expedient in this case to make head piece 85 from a stronger material than that used for the second portion 90. In this way, the barbs are deformed during press-fitting to a lesser degree than the bore of the second portion 90 of piston member 15'.

The embodiment shown here also includes a circumferential edge provided on head piece 85. Said edge is used to hold elastic element 30 in place better, and to improve the seal between elastic element 30 and head piece 85.

Unlike the embodiments discussed so far, the frictionally engaging elastic element 20 has a T-shaped cross-sectional profile here, wherein the horizontal limb of the T forms frictional engagement element 25 and the perpendicular limb of the T forms elastic element 30. A base for elastic element 30 (the inner limb of the H-shaped profile) may be dispensed with here, since there is sufficient fixing due to the first and second parts 85, 90 of piston member 15' being press-fitted into each other. Alternative or additionally, however, a frictionally engaging elastic element having an H-shaped profile as described above may be used, in which case a suitable recess must be provided in the piston member, for example in the form of recesses in the first and the second piston member.

FIG. 11 shows an exploded perspective view of an embodiment of a piston according to the invention, as provided in the embodiment of a syringe shown in FIGS. 10*a*, 10*b* and 10*c*.

Each of the above embodiments shows frictionally engaging elastic elements that are integral in design. However, it should be understood that the invention is not restricted to such integral designs, and that multi-part elements that are suitably combined and which fittingly cooperate may be provided in accordance with the invention.

Figure 12:
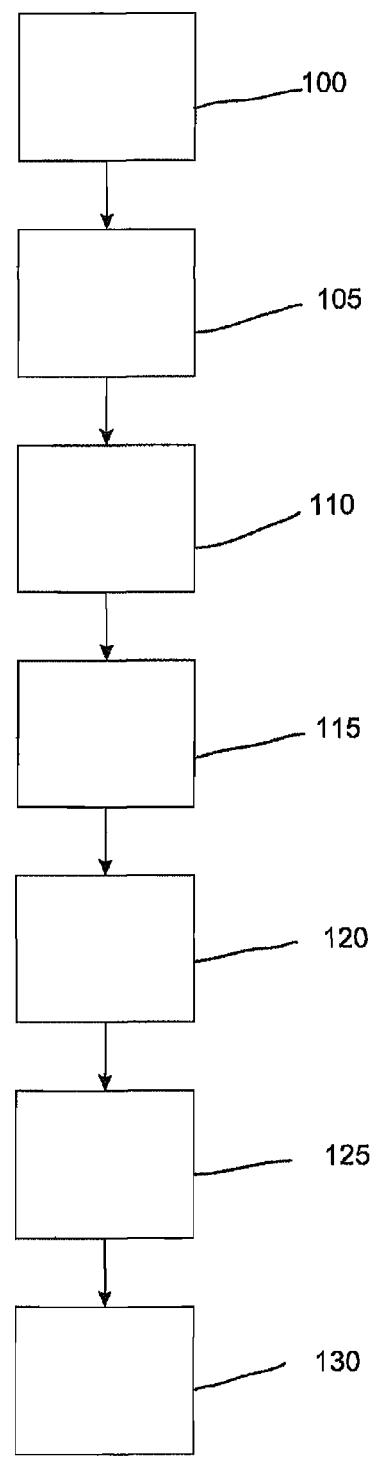

FIG. 12 shows a schematic flow diagram of an embodiment of a method according to the invention.

Insertion of a piston comprising a piston member, an elastic element and a frictional engagement element into a sleeve for accommodating material (step 100) is followed in step 105 by supplying material, for example at the discharge opening of the sleeve, and in step 110 by the piston being retracted. In one possible application of the method according to the invention, retraction in the form of pulling back the piston results in an underpressure being produced inside the sleeve, wherein said underpressure causes the syringe, i.e. the sleeve, to be filled with material. Alternatively or additionally thereto, the piston may also be retracted by being expelled by the material introduced into the syringe.

Instead of pulling in the material by means of an underpressure produced by pulling out the piston, the syringe may be filled by underpressure in the substance being filled into the syringe. In this case, the piston would be pushed out by the liquid or paste flowing into the chamber, until the desired filling level has been reached. This permits syringes according to the invention to be filled industrially in large quantities and in a simple manner.

A syringe filled with material is thus provided. In step 115, the piston of the syringe is impringed with a force, i.e. is pressed into the sleeve, such that the piston penetrates the sleeve. In step 120, the elastic element is tensioned, since the frictional engagement element remainly motionless due to the action of static friction. During further insertion into the sleeve, the frictional engagement element may also be carried along, although tension in the elastic element is maintained due to the action of sliding friction. If the application of a force ends in step 125, the elastic element relaxes in step 130 by expulsion of the piston member, which results in expansion of the inner sleeve chamber. Due to the resultant suction effect, any further and undesired escape of materials from the sleeve is prevented until a force is once again applied.

FIGS. 13*a*, 13*b*, 13*c* respectively show a sixth embodiment of a syringe according to the invention, in a side view, in cross-section and in a sectional enlargement, in a state in which the elastic element is untensioned.

This sixth embodiment largely corresponds to the first embodiment, so a description of identical features can be dispensed with here. The shape of the tip of piston member 15' in the sixth embodiment of the syringe differs from that in the first embodiment, and discharge opening 40 is provided with an attachment which is screwed into the internal thread of discharge opening 40. The difference between the frictionally engaging elastic elements 20 in the first and sixth embodiments is that, in the sixth embodiment, elastic element 30 is embodied with a thicker cross-section in relation to frictional engagement element 25. With an elastic element embodied with a thicker cross-section, it is possible to provide greater stiffness or spring force, similar to the stiffening elements shown in FIGS. 8a-8d, without having to change the choice of materials.

FIG. 14 shows a perspective view of an embodiment of a syringe 1 according to the invention, comprising a piston 15 and sleeve 10 provided with a grip 45.

Discharge opening 40 is provided with an internal thread into which, for example, attachment 95 having the function of a sealing cap can be screwed.

FIGS. 15a, 15b, 15c respectively show a seventh embodiment of a syringe according to the invention, in a side view, in cross-section and in a sectional enlargement, in a state in which the elastic element is untensioned.

This seventh embodiment also corresponds in large measure to the first embodiment. As in the first embodiment, syringe 1 shown in a side view in FIG. 15a likewise comprises a sleeve 10 and a piston 15, said sleeve having a grip 45 at the end opposite the discharge opening, which facilitates operation of syringe 1, especially when pressing in and pulling out piston 15. Starting from the end of sleeve 10 opposite the discharge opening, piston 15 is accommodated inside sleeve 10.

FIG. 15b shows a cross-sectional view of syringe 1 according to the seventh embodiment, in the plane indicated by arrows in FIG. 15a. Syringe 1 comprises sleeve 10 with inner wall 35 defining an inner sleeve chamber 70. Sleeve 10 is also provided with a discharge opening 40. A frictionally engaging elastic element 20 is pulled onto piston member 15' such that piston member 15' extends through the frictionally engaging elastic element 20, which is provided in the form of a profile ring. The tip of piston member 15' is adapted to the shape of the discharge opening in order to minimise the air uptake when material is drawn into syringe 1.

FIG. 15c shows an enlarged detail of FIG. 15b. The enlarged area is shown by a circle in FIG. 15b. As can be seen from FIG. 15c, frictionally engaging elastic element 20 is provided in the form of a profile ring of substantially H-shaped cross-section. Frictionally engaging elastic element 20 is received in a recess 50 of piston member 15' and is thus secured by positive engagement as well (in addition to the frictional engagement between frictionally engaging elastic element 20 and piston member 15') against movement along the longitudinal axis of syringe 1. Piston member 15' also includes an edge 55 which is configured as a stop member for limiting deformation of frictionally engaging elastic element 20 along the longitudinal axis of syringe 1. In the view shown in FIG. 15c, frictionally engaging elastic element 20 is shown in the untensioned state, so edge 55 is at a distance from frictionally engaging elastic element 20.

Frictionally engaging elastic element 20 comprises a frictional engagement element 25 abutting the inner wall 35 of the sleeve, and an elastic element 30. In the substantially H-shaped recess of the profile ring forming the frictionally engaging elastic element, outer profile limb 150 is the frictional engagement element 25, whereas elastic element 30 is formed by the transverse profile limb 140 and the inner profile limb 145. Inner profile limb 145 extends a lesser amount than outer profile limb 150 along the longitudinal axis of syringe 1. In other words, the inner profile limb is shorter than the outer limb, thus resulting in a "distorted" H shape. In addition, transverse profile limb 140 tapers from inner profile limb 145 to outer profile limb 150, that is, radially outwards. By means of this contour, it is possible to achieve a certain progressivity in the elastic properties of the elastic element. Outer profile limb 150, i.e. frictional engagement element 25, is also provided with bevels 135 at the edges of its surface that engages with inner surface 35 of sleeve 10, said bevels allowing simpler insertion of piston member 15', which is provided with frictionally engaging elastic element 20, into sleeve 10. As a result of the profile ring being H-shaped, frictional engagement element 30 has a lip which projects in the direction of inner sleeve chamber 70 (see also FIG. 2d). Frictional engagement element 25 also has a similar lip on the side facing away from inner sleeve chamber 70. Just as in the other corresponding embodiments, this additional sealing lip prevents air from entering when piston 15 is pulled or driven back, for example when filling the syringe.

In one conventional routine, syringes for dispensing pasty material are firstly assembled, after which the piston is then pushed in to its full extent. The syringe is then filled through the discharge opening.

To this end, it is advantageous to push a filling tube into the discharge opening, because the risk of outer contamination with paste components is then at its lowest.

If, using a conventional syringe, the piston is pushed back together with a seal by the paste which is pressed into the syringe, air can be brought in at parts of the periphery. This undesired effect is prevented by providing a sealing lip at the rear as well (i.e. facing away from the discharge opening), for example in the seventh embodiment of the invention.

In addition, frictionally engaging elastic element 20 is symmetrically configured against it being installed the wrong way round, which means there is no need to check its direction of installation when mounting piston member 15' and frictionally engaging elastic element 20. This reduces sources of error during assembly and facilitates assembly in a very general sense.

FIGS. 16a, 16b, 16c respectively show the seventh embodiment of a syringe according to the invention, in a side view, in cross-section and in a sectional enlargement, in a state in which the elastic element is tensioned, similar to FIGS. 15a, 15b and 15c.

The view presented in FIGS. 16a and 16b differs from that shown in FIGS. 16a and 15b in that syringe 1 in FIGS. 16a and 16b is shown in a state in which piston 15 is fully inserted into sleeve 10.

FIG. 16c shows an enlarged view of part of syringe 1 as shown in FIG. 16b, the enlarged section being marked by the circle in FIG. 16b.

In FIG. 16c, piston member 15' with its tip extending through frictional engagement element 20 has been pushed in as far as discharge opening 40. Sleeve 10 is also provided here with a recess 165 for the front portion of frictional engagement element 25 and is configured such that frictionally engaging elastic element 20 abuts the inner sleeve wall in the region of discharge opening 40, in particular with its transverse profile limb or middle limb, due to the tip of piston member 15' abutting discharge opening 40. This reduces any undesired retention of air inside the syringe. In the present case, such abutment also results in the frictionally engaging elastic element becoming tensioned.

Discharge opening 40 is also fitted with an attachment 155 that tapers conically in the direction of the inner sleeve chamber. In other words, said attachment is embodied in such a way that it widens (with taper angle a) from the inside to the outside. This has the advantage that the syringe can be pushed far onto a filling tube 160 without air being pressed undesirably into the inside of the syringe. The last remnant of air is able to escape. Not until filling tube 160 has been pushed through to the end of opening 40 does it sealingly abut around its entire circumference.

One embodiment of the syringe according to the invention has a mainly cylindrical syringe body (sleeve) with an open rear side and a discharge opening. Inside this syringe body there is a translationally displaceable plunger (piston) which sealingly acts against the inner casing surface (inner wall of the sleeve) by means of a seal. The seal and the inner casing surface together have a high friction coefficient, i.e. the seal can only be moved along the inner casing surface by exerting a certain amount of force.

The seal has a thin-walled, elastically deformable region in the form of a membrane (elastic element). When pressure is exerted on the end of the plunger (piston), the latter is moved forwards, and material is extruded from the discharge opening or outlet opening of the syringe chamber (inner sleeve chamber). Since the seal (or more precisely the frictional engagement element abutting the inner wall) is prevented by frictional forces from moving along the inner surface of the syringe wall, the membrane region is elastically stretched first of all, which involves the elastic element being tensioned. This occurs until a point is reached at which the static friction between the seal and the inner wall of the syringe body and the spring force of the membrane are equal. The seal now begins to move slidingly relative to the inner surface of the syringe body.

The amount of tension remaining in the elastic element now depends on the sliding frictional force that arises when the frictional engagement element slides along the inner wall of the sleeve.

If pressure on the plunger is now released, i.e. if the plunger is not inserted any further into the sleeve, no further movement occurs between the outer periphery of the seal and the inner surface of the syringe body. The elastic element remains in a tensioned state that is determined by the sliding friction force that existed between the frictional engagement element and the inner wall of the sleeve. Since the force causing insertion is no longer acting on the piston, the membrane will then retract itself elastically to its original position.

The elastic element thus relaxes, wherein the piston member moves against the direction of discharge, bringing the membrane with it. This results not only in a release of pressure on the material contained in the syringe, but also a reverse suction effect due to the resultant increase in the volume of the inner sleeve chamber. This effect is desirable, in particular because a small amount of material (dental material, for example) is usually found as a small drop at the tip of the needle after application. This drip disappears or is sucked back into the needle due to the aforementioned effect.

In order to limit the elastic deformation of the membrane to an exact value, the plunger may be provided with an edge for limiting its movement. Said edge can move the outer sealing region (the frictional engagement element) even before the spring force of the membrane overcomes the static friction between the seal and the inner surface of the syringe body. In this way, the tensile force of the elastic element can also be limited to a value less than the sliding friction between the inner sleeve wall and the frictional engagement element.

Another advantage results from the fact that, with the aid of said edge, for example, the amount of reverse suction effect can be set independently of production variations in the seal (elasticity of the raw material used, variations in wall thickness).

The invention claimed is:

1. A syringe (1) for dosed dispensing of free-flowing and/or pasty dental materials, said syringe comprising:
    a. a sleeve (10) for accommodating material and
    b. a piston (15) which can be inserted into the sleeve (10), comprising:
        i. a piston member (15') having an axial face and a radial face with an annular recess,
        ii. a frictional engagement element (25) having a first surface which frictionally abuts an inner wall (35) of the sleeve (10) and a second surface is received in said annular recess, and
        iii. an elastic element (30) extending between said first surface and second surface and coupling the frictional engagement element (25) and the piston member (15'),
    wherein the sleeve (10) and the piston (15) inserted into the sleeve (10) define an inner sleeve chamber (70) for accommodating the material,
    wherein the elastic element (30) can be tensioned by relative lag of the first surface of the frictional engagement element (25) in relation to the piston member (15') when the piston (15) and/or the piston member (15') is inserted into the sleeve (10), said frictional engagement element and an inner surface of said sleeve being arranged to provide a frictional force therebetween to cause the relative lag of the first surface of the frictional engagement element and the tensioning of the elastic element,
    wherein by relaxing the elastic element (30) it is possible for the piston member (15') to be expelled at least partially from the sleeve (10) while the frictional engagement element (25) remains motionless, in order to increase the volume of the inner sleeve chamber (70).

2. The syringe (1) of claim 1, wherein the elastic element (30) and the frictional engagement element (25) are jointly and integrally embodied as a frictionally engaging elastic element (20), said frictionally engaging elastic element (20) having a profile ring of substantially H-shaped, T-shaped or L-shaped cross-section.

3. The syringe (1) of claim 2, wherein the frictionally engaging elastic element (20) has a profile ring of substantially H-shaped cross-section, the outer profile limb forming the first surface of the frictional engagement element (25) and the inner transverse profile limb forming the second surface of the elastic element (30), and wherein the elastic element (30) abuts an outer surface of the piston member (15').

4. The syringe (1) of claim 3, wherein the elastic element (30) abuts the piston member (15') in a recess (50) thereof.

5. The syringe (1) of claim 1, wherein the elastic element (30) is spaced apart from the inner wall (35) of the sleeve (10) by the frictional engagement element (25) when the piston (15) is inserted in the sleeve (10).

6. The syringe (1) of claim 1, wherein the elastic element (30) is provided with a central opening, through which a head piece extends, wherein the head piece is coupled to the piston member (15') for mounting the elastic element (30) between the head piece and the piston member (15').

7. The syringe (1) of claim 1, further comprising a limiting means (55, 60, 65) for limiting relative movement between the frictional engagement element (25) and the piston member (15') to a predetermined distance from a relative starting position.

8. The syringe (1) of claim 5, further comprising a first limiting element (55) that limits relative movement when inserting the piston (15) and/or the piston member (15') into the sleeve (10), said first limiting element including a shoulder or edge (55) against which the frictional engagement element (25) and/or the elastic element (30) can abut when the elastic element (30) is tensioned.

9. The syringe (1) of claim 8, further comprising a second limiting element (60, 65) that limits relative movement during at least partial removal of the piston (15) and/or of the piston member (15') from the sleeve (10), wherein the piston member (15') is provided with a first protrusion (60) which engages a second protrusion (65) of the frictional engagement element (25) and/or of the elastic element (30) such that the first protrusion (60) can be placed against the second protrusion (65) on removal of the piston (15) and/or of the piston member (15').

10. The syringe (1) of claim 3, wherein the inner profile limb of the frictionally engaging elastic element (20) extends to a lesser amount in the longitudinal direction of the syringe (1) than the outer profile limb (25).

11. The syringe (1) of claim 3, wherein the transverse profile limb of the frictionally engaging elastic element (20) has a thickness in the longitudinal direction of the syringe (1) that decreases in the outward radial direction.

12. The syringe (1) of claim 1, wherein the sleeve (10) is provided with a discharge opening (40) with a projection for receiving a filling tube, said projection tapering from the outward periphery in the direction of the inner sleeve chamber (70).

13. A piston (15) for a syringe (1) for dosed dispensing of free-flowing and/or pasty dental materials, wherein the piston (15) can be inserted into the syringe (1) and comprises:
    a. a piston member (15') having an annular recess with two opposing axial faces,
    b. a frictional engagement element (25) having a first surface which can frictionally abut an inner wall (35) of a sleeve (10) of the syringe (1) and a second surface is received in said annular recess between said opposing axial faces, and
    c. an elastic element (30) extending between said first surface and second surface and coupling the frictional engagement element (25) and the piston member (15'),
    wherein the piston (15) is configured to define, in combination with the sleeve (10), an inner sleeve chamber (70) for accommodating the material when the piston (15) is inserted into the sleeve (10), said first surface of said frictional engagement element and an inner surface of the syringe being arranged to provide a frictional force therebetween to cause the relative lag of the frictional engagement element and the tensioning of the elastic element between said first surface and second surface,
    wherein the elastic element (30) can be tensioned by relative lag of the frictional engagement element (25) in relation to the piston member (15') when the piston (15) and/or the piston member (15') is inserted into the sleeve (10),
    wherein by relaxing the elastic element (30) it is possible for the piston member (15') to be expelled at least partially from the sleeve (10) while the first surface of the frictional engagement element (25) remains motionless, in order to increase the volume of the inner sleeve chamber (70).

14. A syringe for dosed dispensing of free-flowing and/or pasty dental materials, said syringe comprising: (a) a sleeve for accommodating material and a piston having an annular recess which can be inserted into the sleeve, said annular recess having two opposing axial surfaces, and (b) an elastic element having a first end with a frictional engagement element and a second end received in said annular recess of said piston member between said opposing axial surfaces;
    wherein said elastic element is tensioned by relative lag of said frictional engagement element in relation to the piston when said piston is inserted into said sleeve, and said elastic element is relaxed to at least partially expel said piston from said sleeve while said friction engagement element remains motionless to increase the volume of a chamber within said sleeve.

15. The syringe of claim 1, wherein said elastic member of said friction engagement member is received in said annular recess of said piston.

16. The syringe of claim 1, wherein said piston has a conical shaped axial surface.

17. The piston of claim 13, wherein said elastic member of said friction engagement member is received in an annular recess of said piston.

18. The piston of claim 13, wherein said piston has an axial face at a distal end thereof.

19. The syringe of claim 1, wherein the second surface of the frictional engagement member is retained in said recess during axial movement of said piston member with respect to said sleeve.

20. The syringe of claim 1, wherein said annular recess has two opposing axial faces and said second surface of said frictional engagement element being received between said opposing axial faces.

21. A method for dosed dispensing of free-flowing and/or pasty dental materials, using a syringe (1) comprising:
    a. a sleeve (10) for accommodating material and
    b. a piston (15) which can be inserted into the sleeve (10), comprising:
        i. a piston member (15') having an axial face and a radial face with an annular recess,
        ii. a frictional engagement element (25) having a first surface which frictionally abuts an inner wall (35) of the sleeve (10) and a second surface received in the annular recess, and
        iii. an elastic element (30) extending between the first surface and second surface and coupling the frictional engagement element and the piston member (15'),
    wherein the sleeve (10) and the piston (15) inserted into the sleeve (10) define an inner sleeve chamber (70) for accommodating the material, said method comprising the steps:
    providing (100-110) a syringe (1) filled at least partially with material,
    applying (115) a force to the piston (15) for bringing the piston (15) and/or the piston member (15') into the sleeve (10), to dispense doses of material from the syringe (1),
    tensioning (120) the elastic element (30) by means of a relative lag of the first surface of the frictional engagement element (25) relative to the piston member (15') by inserting the piston into the sleeve, the frictional engagement element and the inner surface of the sleeve being arranged to provide a frictional force therebetween causing the relative lag of the first surface of the frictional engagement element and the tensioning of the elastic element,
    ending (125) the application of force to the piston (15), at least partially expelling (130) the piston member (15') from the sleeve (10) while the frictional engagement element (25) remains motionless, by relaxation of the elastic element (30), wherein an increase in the volume of the inner sleeve chamber (70) is achieved by said expulsion (130), in order to prevent at least partially any undesired further dispensing of material.

\* \* \* \* \*

UNITED STATES PATENT AND TRADEMARK OFFICE
CERTIFICATE OF CORRECTION

PATENT NO. : 8,641,416 B2  
APPLICATION NO. : 12/175934  
DATED : February 4, 2014  
INVENTOR(S) : Uwe Leiner et al.

It is certified that error appears in the above-identified patent and that said Letters Patent is hereby corrected as shown below:

On the Title Page, Item (73), correct the assignee's name to read:

VOCO GmbH, Cuxhaven (DE)

Signed and Sealed this
Thirteenth Day of May, 2014

Michelle K. Lee
*Deputy Director of the United States Patent and Trademark Office*